US008097423B2

(12) United States Patent
Harris

(10) Patent No.: US 8,097,423 B2
(45) Date of Patent: Jan. 17, 2012

(54) MN/CA IX AND BREAST CANCER THERAPY

(75) Inventor: Adrian L. Harris, Oxford (GB)

(73) Assignee: Institute of Virology, Bratislava (SK)

( * ) Notice: Subject to any disclaimer, the term of this patent is extended or adjusted under 35 U.S.C. 154(b) by 0 days.

(21) Appl. No.: 12/181,951

(22) Filed: Jul. 29, 2008

(65) Prior Publication Data

US 2009/0047215 A1 Feb. 19, 2009

(51) Int. Cl.
| | |
|---|---|
| C12Q 1/00 | (2006.01) |
| G01N 1/00 | (2006.01) |
| G01N 21/00 | (2006.01) |
| G01N 21/75 | (2006.01) |
| G01N 33/00 | (2006.01) |
| G01N 33/53 | (2006.01) |
| G01N 33/564 | (2006.01) |
| G01N 33/566 | (2006.01) |
| G01N 33/567 | (2006.01) |
| G01N 33/574 | (2006.01) |
| A01N 61/00 | (2006.01) |
| A61K 38/00 | (2006.01) |

(52) U.S. Cl. ......... 435/7.1; 435/4; 435/7.21; 435/7.23; 436/86; 436/164; 436/174; 436/501; 436/503; 514/1; 514/19.2; 514/19.3; 514/19.4

(58) Field of Classification Search ..................... None
See application file for complete search history.

(56) References Cited

U.S. PATENT DOCUMENTS

| | | | | |
|---|---|---|---|---|
| 5,387,676 | A | 2/1995 | Zavada et al. | 536/23.5 |
| 5,989,838 | A | 11/1999 | Zavada et al. | 435/7.23 |
| 6,004,535 | A | 12/1999 | Zavada et al. | 424/9.34 |
| 2008/0138345 | A1 * | 6/2008 | de Sauvage et al. | 424/139.1 |

FOREIGN PATENT DOCUMENTS

| | | |
|---|---|---|
| WO | WO 93/18152 | 9/1993 |
| WO | WO 95/34650 | 12/1995 |
| WO | WO 03/100029 | 12/2003 |

OTHER PUBLICATIONS

Bartosova et al., "Expression of carbonic anhydrase IX in breast is associated with malignant tissues and is related to overexpression of c-erbB2," *Journal of Pathology*, 197: 314-321 (2002).
Bottini et al., "p53 but not bcl-2 Immunostaining Is Predictive of Poor Clinical Complete Response to Primary Chemotherapy in Breast Cancer Patients," *Clinical Cancer Research*, 6: 2751-2758 (Jul. 2000).
Bottini et al., "Cytotoxic and antiproliferative activity of the single agent epirubicin versus eprirbicin plus tamoxifen as primary chemotherapy in human breast cancer: a single-institution phase III trial," *Endocrine-Related Cancer*, 12: 383-392 (2005).
Brennan et al., "CA IX is an Independent Prognostic Marker in Premenopausal Breast Cancer Patients With One to Three Positive Lymph Nodes and a Putative Marker of Radiation Resistance," *Clinical Cancer Research*, 12(21):6412-6431 (Nov. 1, 2006).
Chia, et al., "Carbonic anhydrase IX (CA IX) is an independent poor prognostic factor in early stage breast cancer: results from a large population-based tissue microarray (TMA) series," *Breast Cancer Research and Treatment*, 88(Supp. 1): S116-S117, Abstract 3015 (2004).
Chia et al., "Prognostic Significance of a Novel Hypoxia-Regulated Marker, Carbonic Anhydrase IX, in Invasive Breast Carcinoma," *Journal of Clinical Oncology*, 19(16): 3660-3668 (Aug. 15, 2001).
Colpaert et al., "The presence of a fibrotic focus in invasive breast carcinoma correlates with the expression of carbonic anhydrase IX and is a marker of hypoxia and poor prognosis," *Breast Cancer Research and Treatment*, 81: 137-147 (2003).
Cooper et al., "Intermittent Hypoxia Induces Proteasome-Dependent Down-Regulation of Estrogen Receptor Alpha in Human Breast Carcinoma," *Clinical Cancer Research*, 10: 8720-8727 (Dec. 15, 2004).
Coradini et al., "Hypoxia and estrogen receptor profile influence the responsiveness of human breast cancer cells to estradiol and antiestrogens," *Cellular and Molecular Life Sciences*, 61: 76-82 (2004).
Dowsett et al., "Response to specific antioestrogen (IC1182780) in tamoxifen-resistant breast cancer," *Lancet*, 345: 525 (Feb. 25, 1995).
Generali et al., "Hypoxia-Inducible Factor-1alpha Expression Predicts a Poor Response to Primary Chemoendocrine Therapy and Disease-Free Survival in Primary Human Breast Cancer," *Clin. Cancer Res.*, 12(15): 4562-4568 (Aug. 1, 2006).
Generali et al, "Role of carbonic anhydrase IX expression in prediction of the efficacy and outcome of primary epirubicin/tamoxifen therapy for breast cancer," *Endocrine-Related Cancer*, 13(3): 921-930 (Sep. 2006).
Generali et al., "Regulation of Hepatocyte Growth Factor Activator Inhibitor 2 by Hypoxia in Breast Cancer," *Clin. Cancer Res.*, 13(2 Pt 1): 550-8 (Jan. 15, 2007).

(Continued)

*Primary Examiner* — Alana H Dent
(74) *Attorney, Agent, or Firm* — Millen, White, Zelano, Branigan, P.C.

(57) ABSTRACT

Herein disclosed are methods that are predictive of resistance to endocrine therapy in an estrogen receptor-positive (ER-positive) breast cancer patient. An exemplary method comprises detecting the overexpression of MN/CA9 gene expression product(s) in a sample from an affected subject, wherein if MN/CA9 is overexpressed, then the subject is considered to have a greater probability of resistance to endocrine therapy, particularly tamoxifen, and a corresponding poorer prognosis if undergoing endocrine therapy, than if MN/CA9 is not over-expressed. MN/CA9 gene expression products useful in the predictive/prognostic methods include MN/CA IX, MN proteins/polypeptides, MN nucleic acids and soluble MN/CA IX antigen (s-CA IX). The methods are useful as an aid in the selection of treatment for a patient with an ER-positive breast tumor. The methods of the invention can be used, for example, to identify those patients requiring additional/alternative therapies, preferably, but not necessarily, therapies that are not affected by acidic pH. The methods also comprise the use of diagnostic/prognostic imaging to detect MN/CA IX in a patient tumor, wherein the presence of MN/CA IX in one or more tumors is indicative of probable resistance to antiestrogen therapy, particularly to tamoxifen.

24 Claims, 2 Drawing Sheets

OTHER PUBLICATIONS

Gerweck, L.E., "Tumor pH: Implications for Treatment and Novel Drug Design," *Seminars in Radiation Oncology*, 8(3): 176-182 (1998).

Harris, A.L., "Hypoxia—A Key Regulatory Factor in Tumour Growth," *Nature Reviews Cancer*, 2: 38-47 (Jan. 2002).

Hornberger et al., "Economic Analysis of Targeting Chemotherapy Using a 21-Gene RT-PCT Assay in Lymph-Node-Negative, Estrogen-Receptor-Positive, Early-Stage Breast Cancer," *American Journal of Managed Care*, 11(5): 313-324 (2005).

Hussain et al., "Hypoxia-regulated carbonic anhydrase IX expression is associated with poor survival in patients with invasive breast cancer," *British Journal of Cancer*, 96(1): 104-109 (Jan. 15, 2007).

Leek et al., "Necrosis correlates with high vascular density and focal macrophage infiltration in invasive carcinoma of the breast," *British Journal of Cancer*, 79(5/6): 991-995 (1999).

Lyman et al., "Impact of a 21-Gene RT-PCR Assay on Treatment Decisions in Early-Stage Breast Cancer," *Cancer*, 109(6): 1011-1018 (Mar. 15, 2007).

Paik, et al., "Multi-gene RT-PCR assay for Predicting recurrence in node negative breast cancer patients—NSABP studies B-20 and B-14," *Breast Cancer Research Treatment.*, 82: S10 (2003).

Pastorekova and Zavada, "Carbonic anhydrase IX (CA IX) as a potential target for cancer therapy," *Cancer Therapy*, 2: 245-262 (2004).

Pastorekova et al., "A Novel Quasi-Viral Agent, MaTu, Is a Two-Component System," *Virology*, 187: 620-626 (1992).

Potter and Harris, "Diagnostic, prognostic and therapeutic implications of carbonic anhydrases in cancer," *British Journal of Cancer*, 89: 2-7 (2003).

Raghunand and Gillies, "pH and chemotherapy," *Novartis Foundation Symposium*, 240: 199-211 (discussion 265-268) (2001).

Raghunand et al., "Enhancement of chemotherapy by manipulation of tumour pH," *British Journal of Cancer*, 80(17): 1005-1011 (1999).

Robertson et al., "Role of Carbonic Anhydrase IX in Human Tumor Cell Growth, Survival, and Invasion," *Cancer Res.*, 64(17): 6160-6165 (Sep. 1, 2004).

Span et al., "Carbonic anhydrase-9 expression levels and prognosis in human breast cancer: association with treatment outcome," *British Journal of Cancer*, 89: 271-276 (2003).

Span et al., "Carbonic anhydrase IX expression is more predictive than prognostic in breast cancer," *British Journal of Cancer*, 96(8): 1309 (Apr. 23, 2007).

Svastova et al. "Hypoxia activates the capacity of tumor-associated carbonic anhydrase IX to acidify extracellular pH," *FEBS Letters*, 577: 439-445 (2004).

Tomes et al., "Necrosis and hypoxia in invasive breast carcinoma," *Breast Cancer Research and Treatment*, 81(1): 61-69 (Sep. 2003).

Trastour et al., "HIF-1alpha and CA IX staining in invasive breast carcinomas: prognosis and treatment outcome," *Int. J. Cancer*, 120(7): 1451-1458 (Apr. 1, 2007).

Vleugel et al., "Differential prognostic impact of hypoxia induced and diffuse HIF-1alpha expression in invasive breast cancer," *Journal of Clinical Pathology*, 58(2): 172-177 (Feb. 2005).

Wykoff et al., "Hypoxia-Inducible Expression of Tumor-Associated Carbonic Anhydrases," *Cancer Research*, 60: 7075-7083 (Dec. 15. 2000).

Wykoff et al., "Expression of the Hypoxia-Inducible and Tumor-Associated Carbonic Anhydrases in Ductal Carcinoma in Situ of the Breast," *American Journal of Pathology*, 158(3): 1011-1019 (2001).

Sargent and Allegra, "Issues in Clinical Trial Design for Tumor Marker Studies," *Seminars in Oncology*, 29(3): 222-230 (Jun. 2002).

Tockman et al., "Considerations in Bringing a Cancer Biomarker to Clinical Application " *Cancer Research* (Suppl.), 52: 2711s-2718s (May 1, 1992).

\* cited by examiner

SEQUENCE LISTING

```
<160> NUMBER OF SEQ ID NOS: 12

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1
acagtcagcc gc atg gct ccc ctg tgc ccc agc ccc tgg ctc cct ctg ttg       51
           Met Ala Pro Leu Cys Pro Ser Pro Trp Leu Pro Leu Leu
               -35                 -30                 -25 atc ccg gcc cct gct cca ggc ctc act gtg caa ctg ctg ctg tca ctg          99
Ile Pro Ala Pro Ala Pro Gly Leu Thr Val Gln Leu Leu Leu Ser Leu
            -20                 -15                 -10 ctg ctt ctg atg cct gtc cat ccc cag agg ttg ccc cgg atg cag gag         147
Leu Leu Leu Met Pro Val His Pro Gln Arg Leu Pro Arg Met Gln Glu
         -5              -1  1                   5 gat tcc ccc ttg gga gga ggc tct tct ggg gaa gat gac cca ctg ggc         195
Asp Ser Pro Leu Gly Gly Gly Ser Ser Gly Glu Asp Asp Pro Leu Gly
     10                  15                  20 gag gag gat ctg ccc agt gaa gag gat tca ccc aga gag gag gat cca         243
Glu Glu Asp Leu Pro Ser Glu Glu Asp Ser Pro Arg Glu Glu Asp Pro
 25                  30                  35                  40 ccc gga gag gag gat cta cct gga gag gag gat cta cct gga gag gag         291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag         339
Asp Leu Pro Glu Val Lys Pro Lys Ser Glu Glu Glu Gly Ser Leu Lys
             60                  65                  70 tta gag gat cta cct act gtt gag gct cct gga gat cct caa gaa ccc         387
Leu Glu Asp Leu Pro Thr Val Glu Ala Pro Gly Asp Pro Gln Glu Pro
         75                  80                  85 cag aat aat gcc cac agg gac aaa gaa ggg gat gac cag agt cat tgg         435
Gln Asn Asn Ala His Arg Asp Lys Glu Gly Asp Asp Gln Ser His Trp
     90                  95                 100 cgc tat gga ggc gac ccg ccc tgg ccc cgg gtg tcc cca gcc tgc gcg         483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc         531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg         579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc         627
Leu Pro Glu Leu Arg Leu Arg Asn Asn Gly His Ser Val Gln Leu Thr
        155                 160                 165 ctg cct cct ggg cta gag atg gct ctg ggt ccc ggg cgg gag tac cgg         675
```

```
                                            Leu Pro Pro Gly Leu Glu Met Ala Leu Gly Pro Gly Arg Glu Tyr Arg
                                                170                 175                 180 gct ctg cag ctg cat ctg cac tgg ggg gct gca ggt cgt ccg ggc tcg              723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt              771
Glu His Thr Val Glu Gly His Arg Phe Pro Ala Glu Ile His Val Val
                205                 210                 215 cac ctc agc acc gcc ttt gcc aga gtt gac gag gcc ttg ggg cgc ccg              819
His Leu Ser Thr Ala Phe Ala Arg Val Asp Glu Ala Leu Gly Arg Pro
                    220                 225                 230 gga ggc ctg gcc gtg ttg gcc gcc ttt ctg gag gag ggc ccg gaa gaa              867
Gly Gly Leu Ala Val Leu Ala Ala Phe Leu Glu Glu Gly Pro Glu Glu
                        235                 240                 245 aac agt gcc tat gag cag ttg ctg tct cgc ttg gaa gaa atc gct gag              915
Asn Ser Ala Tyr Glu Gln Leu Leu Ser Arg Leu Glu Glu Ile Ala Glu
                250                 255                 260 gaa ggc tca gag act cag gtc cca gga ctg gac ata tct gca ctc ctg              963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca             1011
Pro Ser Asp Phe Ser Arg Tyr Phe Gln Tyr Glu Gly Ser Leu Thr Thr
                    285                 290                 295 ccg ccc tgt gcc cag ggt gtc atc tgg act gtg ttt aac cag aca gtg             1059
Pro Pro Cys Ala Gln Gly Val Ile Trp Thr Val Phe Asn Gln Thr Val
                        300                 305                 310 atg ctg agt gct aag cag ctc cac acc ctc tct gac acc ctg tgg gga             1107
Met Leu Ser Ala Lys Gln Leu His Thr Leu Ser Asp Thr Leu Trp Gly
                315                 320                 325 cct ggt gac tct cgg cta cag ctg aac ttc cga gcg acg cag cct ttg             1155
Pro Gly Asp Ser Arg Leu Gln Leu Asn Phe Arg Ala Thr Gln Pro Leu
330                 335                 340 aat ggg cga gtg att gag gcc tcc ttc cct gct gga gtg gac agc agt             1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt             1251
Pro Arg Ala Ala Glu Pro Val Gln Leu Asn Ser Cys Leu Ala Ala Gly
                    365                 370                 375 gac atc cta gcc ctg gtt ttt ggc ctc ctt ttt gct gtc acc agc gtc             1299
Asp Ile Leu Ala Leu Val Phe Gly Leu Leu Phe Ala Val Thr Ser Val
                        380                 385                 390 gcg ttc ctt gtg cag atg aga agg cag cac aga agg gga acc aaa ggg             1347
Ala Phe Leu Val Gln Met Arg Arg Gln His Arg Arg Gly Thr Lys Gly
                395                 400                 405 ggt gtg agc tac cgc cca gca gag gta gcc gag act gga gcc                     1389
Gly Val Ser Tyr Arg Pro Ala Glu Val Ala Glu Thr Gly Ala
410                 415                 420 tagaggctgg atcttggaga atgtgagaag ccagccagag gcatctgagg gggagccggt           1449
aactgtcctg tcctgctcat tatgccactt ccttttaact gccaagaaat tttttaaaat           1509
aaatatttat aat                                                              1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
        -35                 -30                 -25
```

```
Pro Ala Pro Gly Leu Thr Val Gln Leu Leu Ser Leu Leu Leu Leu
    -20             -15              -10

Met Pro Val His Pro Gln Arg Leu Pro Arg Met Gln Glu Asp Ser Pro
 -5              -1  1               5                      10

Leu Gly Gly Gly Ser Ser Gly Glu Asp Asp Pro Leu Gly Glu Glu Asp
             15              20              25

Leu Pro Ser Glu Glu Asp Ser Pro Arg Glu Glu Asp Pro Pro Gly Glu
         30              35              40

Glu Asp Leu Pro Gly Glu Glu Asp Leu Pro Gly Glu Glu Asp Leu Pro
     45              50              55

Glu Val Lys Pro Lys Ser Glu Glu Gly Ser Leu Lys Leu Glu Asp
 60              65              70                      75

Leu Pro Thr Val Glu Ala Pro Gly Asp Pro Gln Glu Pro Gln Asn Asn
             80              85              90

Ala His Arg Asp Lys Glu Gly Asp Asp Gln Ser His Trp Arg Tyr Gly
         95             100             105

Gly Asp Pro Pro Trp Pro Arg Val Ser Pro Ala Cys Ala Gly Arg Phe
        110             115             120

Gln Ser Pro Val Asp Ile Arg Pro Gln Leu Ala Ala Phe Cys Pro Ala
    125             130             135

Leu Arg Pro Leu Glu Leu Leu Gly Phe Gln Leu Pro Pro Leu Pro Glu
140             145             150             155

Leu Arg Leu Arg Asn Asn Gly His Ser Val Gln Leu Thr Leu Pro Pro
            160             165             170

Gly Leu Glu Met Ala Leu Gly Pro Gly Arg Glu Tyr Arg Ala Leu Gln
            175             180             185

Leu His Leu His Trp Gly Ala Ala Gly Arg Pro Gly Ser Glu His Thr
        190             195             200

Val Glu Gly His Arg Phe Pro Ala Glu Ile His Val Val His Leu Ser
    205             210             215

Thr Ala Phe Ala Arg Val Asp Glu Ala Leu Gly Arg Pro Gly Gly Leu
220             225             230             235

Ala Val Leu Ala Ala Phe Leu Glu Glu Gly Pro Glu Glu Asn Ser Ala
            240             245             250

Tyr Glu Gln Leu Leu Ser Arg Leu Glu Glu Ile Ala Glu Glu Gly Ser
            255             260             265

Glu Thr Gln Val Pro Gly Leu Asp Ile Ser Ala Leu Leu Pro Ser Asp
        270             275             280

Phe Ser Arg Tyr Phe Gln Tyr Glu Gly Ser Leu Thr Thr Pro Pro Cys
285             290             295

Ala Gln Gly Val Ile Trp Thr Val Phe Asn Gln Thr Val Met Leu Ser
300             305             310             315

Ala Lys Gln Leu His Thr Leu Ser Asp Thr Leu Trp Gly Pro Gly Asp
            320             325             330

Ser Arg Leu Gln Leu Asn Phe Arg Ala Thr Gln Pro Leu Asn Gly Arg
            335             340             345

Val Ile Glu Ala Ser Phe Pro Ala Gly Val Asp Ser Ser Pro Arg Ala
        350             355             360

Ala Glu Pro Val Gln Leu Asn Ser Cys Leu Ala Ala Gly Asp Ile Leu
        365             370             375

Ala Leu Val Phe Gly Leu Leu Phe Ala Val Thr Ser Val Ala Phe Leu
380             385             390             395

Val Gln Met Arg Arg Gln His Arg Arg Gly Thr Lys Gly Gly Val Ser
            400             405             410
```

Tyr Arg Pro Ala Glu Val Ala Glu Thr Gly Ala
            415                 420

<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3

| | | | | | |
|---|---|---|---|---|---|
| ggatcctgtt | gactcgtgac | cttacccccca | accctgtgct | ctctgaaaca | tgagctgtgt | 60 |
| ccactcaggg | ttaaatggat | taagggcggt | gcaagatgtg | ctttgttaaa | cagatgcttg | 120 |
| aaggcagcat | gctcgttaag | agtcatcacc | aatccctaat | ctcaagtaat | cagggacaca | 180 |
| aacactgcgg | aaggccgcag | ggtcctctgc | ctaggaaaac | cagagacctt | tgttcacttg | 240 |
| tttatctgac | cttccctcca | ctattgtcca | tgaccctgcc | aaatccccct | ctgtgagaaa | 300 |
| cacccaagaa | ttatcaataa | aaaataaat | ttaaaaaaa | aatacaaaaa | aaaaaaaaa | 360 |
| aaaaaaaaa | gacttacgaa | tagttattga | taaatgaata | gctattggta | aagccaagta | 420 |
| aatgatcata | ttcaaaacca | gacggccatc | atcacagctc | aagtctacct | gatttgatct | 480 |
| ctttatcatt | gtcattcttt | ggattcacta | gattagtcat | catcctcaaa | attctccccc | 540 |
| aagttctaat | tacgttccaa | acatttaggg | gttacatgaa | gcttgaacct | actaccttct | 600 |
| ttgcttttga | gccatgagtt | gtaggaatga | tgagtttaca | ccttacatgc | tggggattaa | 660 |
| tttaaacttt | acctctaagt | cagttgggta | gcctttggct | tattttttgta | gctaattttg | 720 |
| tagttaatgg | atgcactgtg | aatcttgcta | tgatagttttt | cctccacact | ttgccactag | 780 |
| gggtaggtag | gtactcagtt | ttcagtaatt | gcttacctaa | gaccctaagc | cctatttctc | 840 |
| ttgtactggc | ctttatctgt | aatatgggca | tatttaatac | aatataattt | ttggagtttt | 900 |
| tttgtttgtt | tgtttgtttg | tttttttgag | acggagtctt | gcatctgtca | tgcccaggct | 960 |
| ggagtagcag | tggtgccatc | tcggctcact | gcaagctcca | cctcccgagt | tcacgccatt | 1020 |
| ttcctgcctc | agcctcccga | gtagctggga | ctacaggcgc | ccgccaccat | gcccggctaa | 1080 |
| ttttttgtat | ttttggtaga | gacggggttt | caccgtgtta | gccagaatgg | tctcgatctc | 1140 |
| ctgacttcgt | gatccacccg | cctcggcctc | ccaaagttct | gggattacag | gtgtgagcca | 1200 |
| ccgcacctgg | ccaatttttt | gagtctttta | aagtaaaaat | atgtcttgta | agctggtaac | 1260 |
| tatggtacat | ttccttttat | taatgtggtg | ctgacggtca | tataggttct | tttgagtttg | 1320 |
| gcatgcatat | gctactttttt | gcagtccttt | cattacattt | ttctctcttc | atttgaagag | 1380 |
| catgttatat | cttttagctt | cacttggctt | aaaaggttct | ctcattagcc | taacacagtg | 1440 |
| tcattgttgg | taccacttgg | atcataagtg | gaaaaacagt | caagaaattg | cacagtaata | 1500 |
| cttgtttgta | agagggatga | ttcaggtgaa | tctgacacta | agaaactccc | ctacctgagg | 1560 |
| tctgagattc | ctctgacatt | gctgtatata | ggcttttcct | ttgacagcct | gtgactgcgg | 1620 |
| actatttttc | ttaagcaaga | tatgctaaag | ttttgtgagc | ctttttccag | agagaggtct | 1680 |
| catatctgca | tcaagtgaga | acatataatg | tctgcatgtt | tccatatttc | aggaatgttt | 1740 |
| gcttgtgttt | tatgctttta | tatagacagg | gaaacttgtt | cctcagtgac | ccaaaagagg | 1800 |
| tgggaattgt | tattggatat | catcattggc | ccacgctttc | tgaccttgga | aacaattaag | 1860 |

```
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
ttgcaatttc cttcttactg tgttaaaaaa aagtatgatc ttgctctgag aggtgaggca    2040
ttcttaatca tgatctttaa agatcaataa tataatcctt tcaaggatta tgtctttatt    2100
ataataaaga taatttgtct ttaacagaat caataaatata atcccttaaa ggattatatc    2160
tttgctgggc gcagtggctc acacctgtaa tcccagcact ttgggtggcc aaggtggaag    2220
gatcaaattt gcctacttct atattatctt ctaaagcaga attcatctct cttccctcaa    2280
tatgatgata ttgacagggt ttgccctcac tcactagatt gtgagctcct gctcagggca    2340
ggtagcgttt tttgttttg tttttgtttt tctttttga cagggtct tgctctgtca    2400 cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc ccaaaatgag gaccgtgtc    2640 ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060 ggctcccta gcagcctgcc ctacctcttt acctgcttcc tggtggagtc agggatgtat    3120
acatgagctg ctttccctct cagccagagg acatgggggg ccccagctcc cctgcctttc    3180
cccttctgtg cctggagctg ggaagcaggc cagggttagc tgaggctggc tggcaagcag    3240
ctgggtggtg ccagggagag cctgcatagt gccaggtggt gccttgggtt ccaagctagt    3300
ccatggcccc gataaccttc tgcctgtgca cacacctgcc cctcactcca ccccatcct    3360 agctttggta tgggggagag ggcacagggc cagacaaacc tgtgagactt tggctccatc    3420
tctgcaaaag ggcgctctgt gagtcagcct gctcccctcc aggcttgctc ctcccccacc    3480
cagctctcgt ttccaatgca cgtacagccc gtacacaccg tgtgctggga caccccacag    3540
tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaagggatga gaactgcaga tgagagaaaa aatgtgcaga cagaggaaaa    4260
```

```
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt ttttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagcaaatga    4920
ttgcaagctg gtaggattgc tgtttggccc acccagctgc ggtgttgagt ttgggtgcgg    4980
tctcctgtgc tttgcacctg cccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacaggggat gaccagagtc attggcgcta tggaggtgag    5160
acacccaccc gctgcacaga cccaatctgg gaacccagct ctgtggatct ccctacagc    5220 cgtccctgaa cactggtccc gggcgtccca cccgccgccc accgtcccac cccctcacct    5280
tttctacccg ggttccctaa gttcctgacc taggcgtcag acttcctcac tatactctcc    5340
caccccaggc gacccgccct ggccccgggt gtcccagcc tgcgcgggcc gcttccagtc    5400
cccggtggat atccgccccc agctcgccgc cttctgcccg gccctgcgcc cctggaact    5460 cctgggcttc cagctcccgc cgctcccaga actgcgcctg cgcaacaatg ccacagtgg    5520 tgaggggtc tccccgccga acttgggga tgggcgggg cgcagggaag ggaaccgtcg    5580
cgcagtgcct gcccggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tggggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtccttttc    5880
agatccacgt ggttcacctc agcaccgcct ttgccagagt tgacgaggcc ttggggcgcc    5940
cgggaggcct ggccgtgttg gccgcctttc tggaggtacc agatcctgga cacccctac    6000 tccccgcttt cccatcccat gctcctcccg gactctatcg tggagccaga gaccccatcc    6060
cagcaagctc actcaggccc ctggctgaca aactcattca cgcactgttt gttcatttaa    6120
cacccactgt gaaccaggca ccagcccca acaaggattc tgaagctgta ggtccttgcc    6180
tctaaggagc ccacagccag tggggaggc tgacatgaca gacacatagg aaggacatag    6240
taaagatggt ggtcacagag gaggtgacac ttaaagcctt cactggtaga aagaaaagg    6300 aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt tttttgtatt tttagtagac agggtttcac catgttggtc aggctggtct    6660
```

```
caaactcctg gcctcaagtg atccgcctga ctcagcctac caaagtgctg attacaagtg      6720
tgagccaccg tgcccagcca cactcactga ttctttaatg ccagccacac agcacaaagt      6780
tcagagaaat gcctccatca tagcatgtca atatgttcat actcttaggt tcatgatgtt      6840
cttaacatta ggttcataag caaaataaga aaaagaata ataaataaaa gaagtggcat       6900
gtcaggacct cacctgaaaa gccaaacaca gaatcatgaa ggtgaatgca gaggtgacac      6960
caacacaaag gtgtatatat ggtttcctgt ggggagtatg tacggaggca gcagtgagtg     7020
agactgcaaa cgtcagaagg gcacgggtca ctgagagcct agtatcctag taaagtgggc     7080
tctctccctc tctctccagc ttgtcattga aaaccagtcc accaagcttg ttggttcgca     7140
cagcaagagt acatagagtt tgaaataata cataggattt taagagggag acactgtctc     7200 taaaaaaaa aacaacagca acaacaaaaa gcaacaacca ttacaatttt atgttccctc      7260
agcattctca gagctgagga atgggagagg actatgggaa ccccttcat gttccggcct      7320 tcagccatgg ccctggatac atgcactcat ctgtcttaca atgtcattcc ccaggagggg    7380
cccggaagaa aacagtgcct atgagcagtt gctgtctcgc ttggaagaaa tcgctgagga     7440
aggtcagttt gttggtctgg ccactaatct ctgtggccta gttcataaag aatcacccct     7500
tggagcttca ggtctgaggc tggagatggg ctccctccag tgcaggaggg attgaagcat     7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc     7680
ccagcacttt gggaggccaa ggcaggtgga tcacgaggtc aagagatcaa gaccatcctg   7740
gccaacatgg tgaaaccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaa aaaaaaaaa gaaaaccaag caaaaaccaa aatgagacaa      7980 aaaaacaag accaaaaaat ggtgtttgga aattgtcaag gtcaagtctg gagagctaaa    8040
ctttttctga gaactgttta tctttaataa gcatcaaata ttttaacttt gtaaatactt     8100
ttgttggaaa tcgttctctt cttagtcact cttgggtcat tttaaatctc acttactcta     8160
ctagaccttt taggtttctg ctagactagg tagaactctg cctttgcatt tcttgtgtct    8220
gttttgtata gttatcaata ttcatattta tttacaagtt attcagatca tttttctttt   8280 tcttttttt tttttttttt tttttacat ctttagtaga gacagggttt caccatattg    8340
gccaggctgc tctcaaactc ctgaccttgt gatccaccag cctcggcctc ccaaagtgct    8400
gggattcatt ttttcttttt aatttgctct gggcttaaac ttgtggccca gcactttatg    8460
atggtacaca gagttaagag tgtagactca gacggtcttt cttctttcct tctcttcctt    8520
cctcccttcc ctcccacctt cccttctctc cttcctttct ttcttcctct cttgcttcct    8580
caggcctctt ccagttgctc caaagccctg tactttttt tgagttaacg tcttatggga    8640
agggcctgca cttagtgaag aagtggtctc agagttgagt taccttggct tctgggaggt    8700
gaaactgtat ccctatacccc tgaagcttta aggggggtgca atgtagatga gccccaaca    8760 tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaaagagg atgtaagatg agatgagaaa    9000
caggagaaga aagaaatcaa ggctgggctc tgtggcttac gcctataatc ccaccacgtt    9060
```

```
gggaggctga ggtgggagaa tggtttgagc ccaggagttc aagacaaggc ggggcaacat      9120
agtgtgaccc catctctacc aaaaaaaccc caacaaaacc aaaaatagcc gggcatggtg      9180
gtatgcggcc tagtcccagc tactcaagga ggctgaggtg ggaagatcgc ttgattccag      9240
gagtttgaga ctgcagtgag ctatgatccc accactgcct accatcttta ggatacattt      9300
atttatttat aaaagaaatc aagaggctgg atggggaata caggagctgg agggtggagc      9360
cctgaggtgc tggttgtgag ctggcctggg acccttgttt cctgtcatgc catgaaccca      9420
cccacactgt ccactgacct ccctagctcc acaccctctc tgacaccctg tggggacctg      9480
gtgactctcg gctacagctg aacttccgag cgacgcagcc tttgaatggg cgagtgattg      9540
aggcctcctt ccctgctgga gtggacagca gtcctcgggc tgctgagcca ggtacagctt      9600
tgtctggttt ccccccagcc agtagtccct tatcctccca tgtgtgtgcc agtgtctgtc      9660
attggtggtc acagcccgcc tctcacatct ccttttttctc tccagtccag ctgaattcct      9720
gcctggctgc tggtgagtct gcccctcctc ttggtcctga tgccaggaga ctcctcagca      9780
ccattcagcc ccagggctgc tcaggaccgc ctctgctccc tctccttttc tgcagaacag      9840
accccaaccc caatattaga gaggcagatc atggtgggga ttcccccatt gtccccagag      9900
gctaattgat tagaatgaag cttgagaaat ctcccagcat ccctctcgca aaagaatccc      9960 ccccccttt tttaaagata gggtctcact ctgtttgccc caggctgggg tgttgtggca    10020
cgatcatagc tcactgcagc ctcgaactcc taggctcagg caatccttc accttagctt    10080 ctcaaagcac tgggactgta ggcatgagcc actgtgcctg gccccaaacg gccctttac    10140 ttggcttta ggaagcaaaa acggtgctta tcttacccct tctcgtgtat ccaccctcat    10200
cccttggctg gcctcttctg gagactgagg cactatgggg ctgcctgaga actcggggca    10260
ggggtggtgg agtgcactga ggcaggtgtt gaggaactct gcagacccct cttccttccc    10320
aaagcagccc tctctgctct ccatcgcagg tgacatccta gccctggttt ttggcctcct    10380
ttttgctgtc accagcgtcg cgttccttgt gcagatgaga aggcagcaca ggtattacac    10440 tgacccttc ttcaggcaca agcttccccc acccttgtgg agtcacttca tgcaaagcgc    10500
atgcaaatga gctgctcctg ggccagtttt ctgattagcc tttcctgttg tgtacacaca    10560 gaagggaac caaggggggt gtgagctacc gcccagcaga ggtagccgag actggagcct    10620
agaggctgga tcttggagaa tgtgagaagc cagccagagg catctgaggg ggagccggta    10680
actgtcctgt cctgctcatt atgccacttc cttttaactg ccaagaaatt ttttaaaata    10740
aatatttata ataaaatatg tgttagtcac cttgttccc caaatcagaa ggaggtattt    10800
gaatttccta ttactgttat tagcaccaat ttagtggtaa tgcatttatt ctattacagt    10860
tcggcctcct tccacacatc actccaatgt gttgctcc                            10898
```

```
<210> SEQ ID NO 4
<211> LENGTH: 540
<212> TYPE: DNA
<213> ORGANISM: Homo sapiens
<220> FEATURE:
<221> NAME/KEY: promoter
<222> LOCATION: (1)..(540)

<400> SEQUENCE: 4
cttgcttttc attcaagctc aagtttgtct cccacatacc cattacttaa ctcaccctcg       60
ggctccccta gcagcctgcc ctacctcttt acctgcttcc tggtggagtc agggatgtat      120
acatgagctg ctttccctct cagccagagg acatgggggg cccagctcc cctgcctttc      180
```

```
ccctttctgtg cctggagctg ggaagcaggc cagggttagc tgaggctggc tgcaagcag      240 ctgggtggtg ccaggagag cctgcatagt gccaggtggt gccttgggtt ccaagctagt       300
ccatggcccc gataaccttc tgcctgtgca cacacctgcc cctcactcca ccccatcct       360 agctttggta tggggagag ggcacagggc cagacaaacc tgtgagactt tggctccatc       420
tctgcaaaag ggcgctctgt gagtcagcct gctcccctcc aggcttgctc ctcccccacc      480
cagctctcgt ttccaatgca cgtacagccc gtacacaccg tgtgctggga caccccacag      540
```

```
<210> SEQ ID NO 5
<211> LENGTH: 59
<212> TYPE: PRT
<213> ORGANISM: Homo sapiens

<400> SEQUENCE: 5

Ser Ser Gly Glu Asp Pro Leu Gly Glu Glu Asp Leu Pro Ser Glu
1               5                   10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
    50                  55

<210> SEQ ID NO 6
<211> LENGTH: 257
<212> TYPE: PRT
<213> ORGANISM: Homo sapiens

<400> SEQUENCE: 6

Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
        35                  40                  45

Leu Gly Phe Gln Leu Pro Pro Leu Pro Glu Leu Arg Leu Arg Asn Asn
    50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
    130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
        195                 200                 205

Thr Val Phe Asn Gln Thr Val Met Leu Ser Ala Lys Gln Leu His Thr
```

```
            210                 215                 220
Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

<210> SEQ ID NO 7
<211> LENGTH: 37
<212> TYPE: PRT
<213> ORGANISM: Homo sapiens

<400> SEQUENCE: 7

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
                20                  25                  30

Met Pro Val His Pro
            35

<210> SEQ ID NO 8
<211> LENGTH: 377
<212> TYPE: PRT
<213> ORGANISM: Homo sapiens

<400> SEQUENCE: 8

Gln Arg Leu Pro Arg Met Gln Glu Asp Ser Pro Leu Gly Gly Gly Ser
1               5                   10                  15

Ser Gly Glu Asp Asp Pro Leu Gly Glu Glu Asp Leu Pro Ser Glu Glu
                20                  25                  30

Asp Ser Pro Arg Glu Glu Asp Pro Pro Gly Glu Glu Asp Leu Pro Gly
            35                  40                  45

Glu Glu Asp Leu Pro Gly Glu Glu Asp Leu Pro Glu Val Lys Pro Lys
50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
            115                 120                 125

Ile Arg Pro Gln Leu Ala Ala Phe Cys Pro Ala Leu Arg Pro Leu Glu
130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
    210                 215                 220

Val Asp Glu Ala Leu Gly Arg Pro Gly Gly Leu Ala Val Leu Ala Ala
225                 230                 235                 240
```

```
Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
            260                 265                 270

Gly Leu Asp Ile Ser Ala Leu Leu Pro Ser Asp Phe Ser Arg Tyr Phe
        275                 280                 285

Gln Tyr Glu Gly Ser Leu Thr Thr Pro Pro Cys Ala Gln Gly Val Ile
    290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp
    370                 375

<210> SEQ ID NO 9
<211> LENGTH: 20
<212> TYPE: PRT
<213> ORGANISM: Homo sapiens

<400> SEQUENCE: 9

Ile Leu Ala Leu Val Phe Gly Leu Leu Phe Ala Val Thr Ser Val Ala
1               5                   10                  15

Phe Leu Val Gln
            20

<210> SEQ ID NO 10
<211> LENGTH: 25
<212> TYPE: PRT
<213> ORGANISM: Homo sapiens

<400> SEQUENCE: 10

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 11
<211> LENGTH: 19
<212> TYPE: DNA
<213> ORGANISM: Homo sapiens

<400> SEQUENCE: 11
aggaggatct gcccagtga                                              19

<210> SEQ ID NO 12
<211> LENGTH: 19
<212> TYPE: DNA
<213> ORGANISM: Homo sapiens

<400> SEQUENCE: 12
gccaatgact ctggtcatc                                              19
```

MN/CA IX AND BREAST CANCER THERAPY

FIELD OF THE INVENTION

The present invention is in the general area of medical genetics and in the fields of biochemical engineering, immunochemistry and oncology. More specifically, it relates to the MN gene—a cellular gene considered to be an oncogene, known alternatively as MN/CA9, CA9, or carbonic anhydrase 9, which gene encodes the oncoprotein now known alternatively as the MN protein, the MN/CA IX isoenzyme, MN/CA IX, carbonic anhydrase IX, CA IX, the MN/G250 or the G250 protein.

More specifically, the instant invention concerns methods of detecting, or detecting and quantitating, MN antigen and/or MN gene expression in tumors, tumor samples or body fluids, of estrogen receptor-positive (ER-positive) breast cancer patients, wherein said methods provide the basis for predicting patient resistance to endocrine therapy for breast cancer, and for making clinical decisions concerning cancer treatment. The methods in one aspect are particularly directed to predicting the resistance of ER-positive breast cancer patients to antiestrogens, such as tamoxifen.

REFERENCE TO SEQUENCE LISTING

The Sequence Listing, filed electronically herewith and identified as MST-5298-1-SEQ-LISTING, was created on Jul. 24, 2008, is 32.4 kb in size and is hereby incorporated by reference.

BACKGROUND OF THE INVENTION

As indicated above, the MN gene and protein are known by a number of alternative names, which names are used herein interchangeably. The MN protein was found to bind zinc and have carbonic anhydrase (CA) activity and is now considered to be the ninth carbonic anhydrase isoenzyme—MN/CA IX or CA IX [Opavsky et al., "Human MN/CA9 gene, a novel member of the carbonic anhydrase family: structure and exon to protein domain relationships," *Genomics*. 33: 480-487 (1996)]. According to the carbonic anhydrase nomenclature, human CA isoenzymes are written in capital Roman letters and numbers, whereas their genes are written in italic letters and Arabic numbers. Alternatively, "MN" is used herein to refer either to carbonic anhydrase isoenzyme IX (CA IX) proteins/polypeptides, or carbonic anhydrase isoenzyme 9 (CA9) gene, nucleic acids, cDNA, mRNA etc. as indicated by the context.

The MN protein has also been identified with the G250 antigen. Uemura et al. ["Expression of Tumor-Associated Antigen MN/G250 in Urologic Carcinoma: Potential Therapeutic Target," *J. Urol.* 157 (4 Suppl.): 377 (Abstract 1475; 1997)] states: "Sequence analysis and database searching revealed that G250 antigen is identical to MN, a human tumor-associated antigen identified in cervical carcinoma (Pastorek et al., 1994)."

Zavada et al., International Publication No. WO 93/18152 (published Sep. 16, 1993) and U.S. Pat. No. 5,387,676 (issued Feb. 7, 1995) describe the discovery of the MN gene and protein. The MN gene was found to be present in the chromosomal DNA of all vertebrates tested, and its expression to be strongly correlated with tumorigenicity. In general, oncogenesis may be signified by the abnormal expression of CA IX protein. For example, oncogenesis may be signified: (1) when CA IX protein is present in a tissue which normally does not express CA IX protein to any significant degree; (2) when CA IX protein is absent from a tissue that normally expresses it; (3) when CA9 gene expression is at a significantly increased level, or at a significantly reduced level from that normally expressed in a tissue; or (4) when CA IX protein is expressed in an abnormal location. WO 93/18152 further discloses, among other MN-related inventions, MN/CA IX-specific monoclonal antibodies (MAbs), including the M75 MAb and the VU-M75 hybridoma that secretes the M75 MAb. The M75 MAb specifically binds to immunodominant epitopes on the proteoglycan (PG) domain of MN/CA IX.

Zavada et al., International Publication No. WO 95/34650 (published Dec. 21, 1995) provides in FIG. 1 the nucleotide sequence for a full-length MN cDNA [SEQ ID NO: 1] clone isolated as described therein, and the amino acid sequence [SEQ ID NO: 2] encoded by that MN cDNA. WO 95/34650 also provides in FIG. 3A-F a 10,898 base pair (bp) complete genomic sequence of MN [SEQ ID NO: 3], and in FIG. 6 the nucleotide sequence for the MN promoter [SEQ ID NO: 4]. Those MN cDNA, amino acid, genomic, and promoter sequences are incorporated by reference herein.

Zavada et al., International Publication No. WO 03/100029 (published Dec. 4, 2003) discloses among other MN-related inventions, MN/CA IX-specific MAbs that are directed to non-immunodominant epitopes, including those on the carbonic anhydrase (CA) domain of MN/CA IX. An example of such a MN/CA IX-specific MAb is the V/10 MAb, secreted from the V/10-VU hybridoma.

The MN protein is now considered to be the first tumor-associated carbonic anhydrase isoenzyme that has been described. The carbonic anhydrase family (CA) includes twelve catalytically active zinc metalloenzymes involved in the reversible hydration-dehydration of carbon dioxide: $CO_2 + H_2O \Leftrightarrow HCO_3^- + H^+$. CAs are widely distributed in different living organisms. The CAs participate in a variety of physiological and biological processes and show remarkable diversity in tissue distribution, subcellular localization, and biological functions, including pH regulation, $CO_2$ and $HCO_3$ transport, and water and electrolyte balance. [Parkkila and Parkkila, *Scand J Gastroenterol.*, 31: 305-317 (1996); Potter and Harris, *Br J Cancer*, 89: 2-7 (2003); Wingo et al., *Biochem Biophys Res Commun*, 288: 666-669 (2001); Christianson and Cox, *Ann Rev Biochem*, 68: 33-57 (1999); Supuran et al., *Curr Med Chem Cardiov Hemat Agents*, 2: 51-70 (2004).] CA IX is a glycosylated transmembrane CA isoform with a unique N-terminal proteoglycan-like extension [Opavsky et al. (1996)]. Through transfection studies it has been demonstrated that CA IX can induce the transformation of 3T3 cells [Opavsky et al. (1996)].

Many studies, using the MN-specific monoclonal antibody (MAb) M75, have confirmed the diagnostic/prognostic utility of MN in diagnosing/prognosing precancerous and cancerous cervical lesions [Liao et al., *Am. J. Pathol.*, 145: 598-609 (1994); Liao and Stanbridge, *Cancer Epidemiology, Biomarkers & Prevention*, 5: 549-557 (1996); Brewer et al., *Gynecologic Oncology* 63: 337-344 (1996)]. Immunohistochemical studies with the M75 MAb of cervical carcinomas and a PCR-based (RT-PCR) survey of renal cell carcinomas have identified MN expression as closely associated with those cancers and confirm MN's utility as a tumor biomarker [Liao et al. (1994); Liao and Stanbridge (1996); McKiernan et al., *Cancer Res.* 57: 2362-2365 (1997)]. In various cancers (notably uterine cervical, ovarian, endometrial, renal, bladder, breast, colorectal, lung, esophageal, head and neck and prostate cancers, among others), CA IX expression is increased and has been correlated with the microvessel density and the levels of hypoxia in some tumors [Koukourakis et al. (2001); Giatromanolaki et al. (2001)].

In tissues that normally do not express MN protein, CA IX positivity is considered to be diagnostic for preneoplastic/neoplastic diseases, such as, lung, breast and cervical precancers/cancers [Swinson et al. (2003); Chia et al. (2001); Loncaster et al. (2001)], among other precancers/cancers. Very few normal tissues have been found to express MN protein to any significant degree; those MN-expressing normal tissues include the human gastric mucosa and gallbladder epithelium, and some other normal tissues of the alimentary tract [Pastorekova and Zavada, "Carbonic anhydrase IX (CA IX) as a potential target for cancer therapy," *Cancer Therapy*, 2: 245-262 (2004); Pastorekova et al., "Carbonic Anhydrase IX: Analysis of stomach complementary DNA sequence and expression in human and rat alimentary tracts," *Gastroenterology*, 112: 398-408 (1997); Leppilampi et al., "Carbonic anhydrase isozymes IX and XII in gastric tumors," *World J Gastroenterol*, 9: 1398-1403 (2003)].

MN/CA IX and Hypoxia

Recent studies have revealed that CA IX not only participates in cell adhesion and pH regulation, but also can be induced in hypoxia via the HIF-1 protein binding to the hypoxia-responsive element of the MN promoter [Svastova et al., *Exp Cell Res*, 290: 332-345 (2003); Wykoff et al., *Cancer Res*, 60: 7075-7083 (2000)]. Hypoxia is a common feature in solid tumors. It is a pathophysiologic consequence of a structurally and functionally disturbed microcirculation and the deterioration of oxygen diffusion conditions [Höckel and Vaupel (2001)]. Tumor hypoxia has long been known to be associated with poor survival in cancer patients, since it may contribute to the development of more malignant tumor phenotypes and increase tumor invasiveness and metastatic potential [Harris (2002)]. Hypoxia also has an important role in the development of resistance to chemotherapy and radiotherapy [Höckel et al. (1996)].

It is recognized that tumor cells under hypoxic conditions maintain a low extracellular pH (pHe) and a high intracellular pH [Svastova et al. (2004)]. This confers a survival advantage by possible prevention of tumor cell apoptosis and facilitates the local invasiveness of the tumor by breakdown of the extracellular matrix [Svastova et al. (2004)]. In addition, the acidic tumor microenvironment may reduce the uptake of drugs which are weak bases and hence ionized at acid pH [Gerweck and Seetharaman (1996); Raghunand et al., (1999); Raghunand and Gillies (2001)]. For example, under some circumstances, an acidic tumor environment may indicate against the use of anthracyclines.

MN/CA IX Hypoxic Regulation

The transcription of the MN gene is negatively regulated by wild-type von Hippel-Lindau tumor suppressor gene in transfected renal cell carcinoma cells [Ivanov et al., *Proc Natl Acad Sci* (USA), 95: 12596-12601 (1998)]. The protein product of the von Hippel-Lindau tumor suppressor gene interacts with the ubiquitin ligase complex that is responsible for targeting HIF-1α for oxygen-dependent proteolysis [Maxwell et al., *Nature*, 399: 271-275 (1999); Jaakkola et al., *Science*, 292: 468-472 (2001)]. Thus, low levels of oxygen lead to stabilization of HIF-1α, which in turn leads to the increased expression of MN [Wykoff et al. (2000)]. Areas of high expression of MN in cancers are linked to tumor hypoxia as reported in many cancers, and incubation of tumor cells under hypoxic conditions leads to the induction of MN expression [Wykoff et al. (2000); Koukourakis et al., *Clin Cancer Res*, 7: 3399-3403 (2001); Giatromanolaki et al., *Cancer Res*, 61: 7992-7998 (2001); Swinson et al., *J Clin Oncoli*, 21: 473-482 (2003); Chia et al., *J Clin Oncol*, 19: 3660-3668 (2001); Loncaster et al., *Cancer Res*, 61: 6394-6399 (2001)]. Expression of MN/CA IX is localized to the perinecrotic area of tumors and has been observed to start at a median distance of 80 μm from a blood vessel, where the oxygen tension drops to 1%, in head and neck squamous cell carcinoma [Beasley et al. (2001)].

MN/CA IX and Breast Cancer Therapy

It has been shown that MN/CA IX can acidify the pHe of tumor cells in a culture medium and downregulation reduces the survival of breast tumor cells under hypoxic conditions [Potter and Harris (2003)]. In three studies, the expression of MN/CA IX was associated with poor prognosis independent of the other commonly recognized prognostic parameters such as tumor (T) status, node (N) status, tumor grade, estrogen receptor (ER), and c-erbB2 expression in breast cancer patients [Chia et al. (2001); Bartosova et al. (2002); Span et al. (2003)]. All those studies involved heterogeneous patient populations submitted postoperatively to different treatment strategies (radiotherapy, chemotherapy, and endocrine therapy) or no therapy.

Primary chemotherapy administered to the breast cancer patients is a useful model to identify baseline features able to predict which patients are most likely to benefit from the cytotoxic treatment and is a way to study new biological markers in relation to the predictive information they provide. In addition, tumor biopsy specimens obtained in matched pair cases at diagnosis and definitive surgery provide valuable information on the interaction between biological markers and treatment.

For example, breast cancer patients are routinely tested for the presence or absence of the estrogen receptor in an attempt to predict whether the patients will be resistant or responsive to tamoxifen [Nolvadex®; AstraZeneca], a nonsteroidal anti-estrogen that is currently the most widely used breast cancer treatment. Based on the current test, cancer patients who test positive for the presence of estrogen receptors ("ER positive") are typically prescribed tamoxifen. However, a significant number of ER positive patients are in fact resistant to tamoxifen. Therefore, administration of tamoxifen to a patient who is resistant to its benefits may cause delay by preventing the patient from undergoing more effective treatments. Further, tamoxifen administration has been associated with an increased risk of endometrial cancer. An accurate determination of whether a patient will be susceptible or resistant to the antineoplastic effects of tamoxifen administration, before embarking on such a treatment course, would be a valuable diagnostic tool. Due in large part to the limited ability of clinical criteria to assess accurately an individual's risk, many patients continue to be overtreated or undertreated [Lyman et al. (2007)].

Commercialized multigene assays have been developed to predict clinical outcome for breast cancer. For example, the Oncotype DX™ diagnostic assay was recently developed by Genomic Health, and tests for 21 genes, including genes associated with proliferation, estrogen and HER-2 activity, invasion, as well as five control genes. This assay provides a recurrence score for lymph node negative breast cancer patients with estrogen receptor positive tumors that have received adjuvant tamoxifen [Paik et al., *Breast Cancer Res. Treat.*, 82: S10 (2003)]. However, such a multigene test is expensive: the cost of Oncotype DX™ patient testing was estimated in 2005 as $3,450 per patient [Hornberger et al., *Am J Manag Care*, 11(5): 317 (2005)]. It would be useful to have an assay to predict clinical outcome for tamoxifen treatment of patients with breast cancer, that was relatively inexpensive and could be performed routinely, based on the detection of expression of only one gene, and which could be also performed by immunohistochemistry.

Disclosed herein are methods wherein MN overexpression is shown to be useful as a prognostic marker for estrogen receptor (ER) positive breast cancer, particularly for those patients who are treated with, or under consideration for treatment with, endocrine therapy, particularly tamoxifen therapy. MN positive expression in ER-positive breast cancer patients treated with tamoxifen was found to be a poor prognostic factor, and conversely MN negative expression was found to be a good prognostic factor. The prognostic methods disclosed herein detect MN overexpression, and can identify high-risk estrogen receptor positive breast cancer patients who could benefit from additional and/or alternative therapies, such as adjuvant chemotherapy or immunotherapy and MN-targeted therapies, among other appropriate therapies.

SUMMARY OF THE INVENTION

The present invention relates to methods of predicting resistance to endocrine therapy, particularly tamoxifen therapy, in a patient afflicted with estrogen receptor (ER) positive breast cancer, comprising detecting, or detecting and quantitating, MN/CA9 overexpression in a sample taken from said patient. The breast cancer patient can be a vertebrate, preferably a mammal, and more preferably a human.

The methods comprise detecting, or detecting and quantitating, MN/CA9 gene expression product(s) in a sample taken from the breast cancer patient, and determining that the patient has greater probability of resistance to endocrine therapy, and/or a poorer prognosis if undergoing endocrine therapy, if the presence, level, intensity and/or extent of MN/CA9 gene expression product(s) indicates that MN/CA9 is overexpressed in said patient sample, than if said MN/CA9 product is not overexpressed in said patient sample. In addition to predicting clinical outcome, the methods of the present invention can also identify high-risk ER-positive breast cancer patients in need of adjuvant chemotherapy, and/or identify candidates for MN-targeted therapies, among other courses of treatment.

In a preferred embodiment of the invention, the MN/CA9 gene expression product is MN antigen, and the methods comprise immunologically detecting MN antigen in a breast tumor tissue sample taken from an ER-positive breast cancer patient. In an alternate preferred embodiment of the invention, the MN/CA9 gene expression product is soluble MN/CA IX antigen (s-CA IX), and the methods comprise immunologically detecting s-CA IX in a body fluid sample, preferably a blood, serum, or breast exudate sample, taken from an ER-positive breast cancer patient.

Preferably, said sample is taken from said breast cancer, or from a metastatic lesion derived from said breast cancer. Such samples can be, for example, tissue specimens, tissue extracts, body fluids, cells, cell lysates and cell extracts, among other samples. Preferred tissue specimens to assay by immunohistochemical staining, for example, include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Preferred tissue samples are formalin-fixed, paraffin-embedded tissue samples.

A poorer prognosis can be measured, for example, in terms of shortened disease-free survival (DFS), shortened overall survival (OS), increased risk of recurrence, and/or increased risk of metastasis, among other clinical endpoints. Preferably, said poorer prognosis is measured in terms of shortened disease-free survival (DFS) or shortened overall survival (OS).

Said endocrine therapy comprises or consists of the use of an antiestrogen or estrogen lowering drug, or drug that modifies endocrine environment. Preferably, said endocrine therapy is a selective estrogen receptor modulator (SERM), a pure antiestrogen, a steroidal aromatase inhibitor, a nonsteroidal aromatase inhibitor, or estrogen. Preferably, said endocrine therapy is selected from the group consisting of tamoxifen, raloxifene, toremifene, fulvestrant, exemestane, letrozole or anastrozole. More preferably, said antiestrogen is tamoxifen.

In one aspect, the invention concerns methods of predicting resistance to endocrine therapy in a breast cancer patient with an ER-positive breast tumor, wherein an exemplary method comprises:

(a) obtaining a breast tumor tissue sample from said patient; and (b) detecting MN/CA9 gene product overexpression in said sample, wherein said MN/CA9 gene product overexpression is indicative of a greater probability of resistance in said patient to said endocrine therapy, than if said MN/CA9 gene product is not overexpressed;

wherein said MN/CA9 gene product is encoded by a nucleotide sequence selected from the group consisting of:

(1) SEQ ID NO: 1's coding region;

(2) nucleotide sequences that hybridize under stringent hybridization conditions of 50% formamide at 42 degree C. to complement of SEQ ID NO: 1's coding region; and (3) nucleotide sequences that differ from SEQ ID NO: 1's coding region or from the nucleotide sequences of (2) in codon sequence due to the degeneracy of the genetic code. SEQ ID NO: 1 is the full-length MN cDNA as disclosed in Zavada et al. WO 95/34650, supra.

Preferred assays to be used according to the methods of the invention to detect said MN/CA9 gene product overexpression in detecting step (b) are those wherein said MN/CA9 gene product comprises MN/CA IX or a MN protein, and said assays are selected from the group consisting of Western blots, enzyme-linked immunosorbent assays, radioimmunoassays, competition immunoassays, dual antibody sandwich assays, immunohistochemical staining assays, agglutination assays, and fluorescent immunoassays. More preferably, said MN/CA9 gene product detecting step (b) comprises the use of immunohistochemical staining of tumor cells in a patient sample, wherein if any cells in said sample are immunoreactive, concluding that said patient has a poorer prognosis than if no cells in said sample are immunoreactive. Preferably, the detecting step (b) comprises determining the intensity of MN/CA IX staining, wherein any conventionally detectable MN/CA IX staining is considered to represent MN/CA IX overexpression. Still more preferably, said detecting step (b) comprises the use of a MN/CA IX-specific monoclonal antibody, preferably the M75 MAb secreted by the hybridoma VU-M75 which has Accession No. ATCC HB 11128.

In an alternative preferred embodiment, preferred assays to be used according to the methods of the invention in said MN/CA9 gene overexpression detecting step (b) are nucleic acid-based assays, wherein said MN/CA9 gene expression product comprises a mRNA encoding MN/CA IX, a MN protein, or a MN polypeptide or a cDNA complementary to mRNA encoding MN/CA IX, a MN protein, or a MN polypeptide. Preferably, said detecting step (b) is by in situ hybridization, Northern blotting, PCR, RT-PCR, real-time PCR, or by quantitative real-time RT-PCR. Nucleic acid-based assays for detecting, or detecting and quantitating, MN/CA9 gene overexpression in vertebrate samples are described in greater detail elsewhere, for example, in Zavada et al., U.S. Pat. No. 7,186,514.

An exemplary and preferred method of predicting resistance to endocrine therapy in a breast cancer patient with an ER-positive breast tumor comprises:

(a) obtaining a breast tumor tissue sample from said patient; and (b) determining MN/CA IX positivity or MN/CA IX negativity in said sample, wherein MN/CA IX positivity is indicative of a greater probability of resistance to said endocrine therapy than MN/CA IX negativity; and wherein "MN/CA IX positivity" indicates MN/CA IX overexpression. Said endocrine therapy comprises or consists of the use of an antiestrogen or estrogen lowering drug, or drug that modifies the endocrine environment. Preferably, said endocrine therapy is a selective estrogen receptor modulator (SERM), a pure antiestrogen, a steroidal aromatase inhibitor, a nonsteroidal aromatase inhibitor, or estrogen. Preferably, said endocrine therapy is selected from the group consisting of tamoxifen, raloxifene, toremifene, fulvestrant, exemestane, letrozole or anastrozole. More preferably, said antiestrogen is tamoxifen.

An exemplary and particularly preferred method which is predictive of resistance to endocrine therapy, and/or prognostic if undergoing endocrine therapy, for ER-positive breast cancer afflicting a patient comprises:

(a) obtaining a neoplastic sample from said patient;

(b) detecting MN/CA IX in said sample, comprising the use of immunohistochemical staining with MN/CA IX-specific antibody;

(c) determining an MN/CA IX immunoreactivity score of cells in said sample, wherein said sample is assigned an immunoreactivity score with
 a value of 0 (zero) if no staining,
 a value of 1 if weak staining, or
 a value of 2 if strong staining;
and
wherein if the immunoreactivity score of the sample is greater than 0 (zero), concluding in step (d) that said patient has a greater probability of resistance to said endocrine therapy, and/or has a poorer prognosis if undergoing endocrine therapy, than if said immunoreactivity score is 0 (zero).

In another aspect, this invention is directed to a method of predicting resistance to endocrine therapy in an ER-positive breast cancer patient, comprising the use of assays to detect or to detect and quantify soluble MN/CA IX antigen (s-CA IX). An exemplary and preferred method which is predictive of resistance to endocrine therapy for ER-positive breast cancer afflicting a patient comprises:

(a) obtaining a body fluid sample from said patient; and (b) immunologically detecting s-CA IX in said sample, wherein s-CA IX in said sample is indicative of a greater probability of resistance of said patient to said endocrine therapy, than if s-CA IX is not detected in said sample. Preferably, said endocrine therapy comprises or consists of the use of an antiestrogen. More preferably, said antiestrogen is tamoxifen. Exemplary assays for detecting, or detecting and quantitating, s-CA IX overexpression in vertebrate body fluid samples are described in greater detail elsewhere [e.g., Pastorek et al., US Patent Application No. US2005031623 A1; Zavada et al., Br J Cancer, 89(6): 1067-71 (2003)].

Further, this invention concerns the coexpression of MN/CA IX and HER-2/neu/c-erbB-2 ("HER-2"), and diagnostic/prognostic and therapeutic methods in parallel with and/or alternative to those targeting MN/CA9. Particularly preferred are assays to detect both s-CA IX [the predominant species being the MN/CA IX extracellular domain (50/54 kilodaltons)] and the HER-2 ectodomain ("p100") in the same body fluid sample from an ER-positive breast cancer patient. Backup therapeutic methods targeting MN/CA IX/CA9 and/or HER-2 can be used for patients not responding to, or having low probability of responding to, endocrine therapy. Such integrated diagnostic/prognostic and therapeutic methods with MN/CA IX/CA9 and HER-2 as targets can provide clinicians with more comprehensive resources to help ER-positive breast cancer patients.

The invention also concerns a method of predicting resistance to an endocrine therapy, preferably an antiestrogen therapy, in a breast cancer patient with an ER-positive breast tumor, comprising the use of diagnostic/prognostic imaging to detect the presence or absence of MN/CA IX in one or more tumors in said patient, wherein the presence of MN/CA IX in said one or more tumors is indicative that said patient has a greater probability of resistance to said endocrine therapy, preferably said antiestrogen therapy, than if MN/CA IX is absent in said one or more tumors. Said one or more tumors may be primary breast tumor(s) and/or metastatic tumor(s). Preferably, said diagnostic/prognostic imaging comprises the use of labeled MN/CA IX-specific antibodies or labeled MN/CA IX-specific inhibitors, such as MN/CA IX-specific sulfonamide inhibitors, preferably aromatic and heterocyclic sulfonamides.

Further, the methods of the invention can be used as an aid in the selection of treatment for an ER-positive breast cancer patient. The methods of the invention can be used, for example, to identify those subsets of patients with a higher than average probability of resistance to one or more endocrine therapies, in order to establish additional or alternative therapy regimens. In one embodiment of the invention, if MN/CA9 gene product overexpression is detected in a tumor, or in a metastasis of said tumor, obtained from an ER-positive breast cancer patient, said MN/CA9 gene product overexpression is indicative of greater resistance to antiestrogen therapy, preferably tamoxifen, than if said MN/CA9 gene product is not overexpressed, and therefore indicates that said patient should be administered additional or alternative therapy, preferably a therapy that is not substantially inhibited by acidic pH. Said MN/CA9 gene expression product may comprise, for example, MN/CA IX, a MN protein or a MN polypeptide, an mRNA encoding MN/CA IX, a MN protein or a MN/polypeptide, or a cDNA encoding MN/CA IX, a MN protein or a MN polypeptide. Preferably, said additional or alternative therapy is selected from adjuvant chemotherapy, alternative endocrine therapy, or MN-targeted therapy. More preferably, said adjuvant chemotherapy is a taxane, preferably paclitaxel or docetaxel. Alternatively, said additional or alternative therapy is an anthracycline, preferably epirubicin or doxorubicin. It may be preferred under certain circumstances that the additional or alternative therapy is one that is not affected by acidic pH, whether the effect is on uptake, activity or any other mechanism.

Aspects of the instant invention disclosed herein are described in more detail below.

REFERENCES

1. Bartosova et al., "Expression of carbonic anhydrase IX in breast is associated with malignant tissues and is related to overexpression of c-erbB2," *Journal of Pathology*, 197: 314-321 (2002).

2. Beasley et al., "Carbonic anhydrase IX, an endogenous hypoxia marker, expression in head and neck squamous cell carcinoma and its relationship to hypoxia, necrosis, and microvessel density," *Cancer Research*, 61: 5262-5267 (2001).

3. Bottini et al., "p53 but not bcl-2 immunostaining is predictive of poor clinical complete response to primary chemotherapy in breast cancer patients," *Clinical Cancer Research*, 6: 2751-2758 (2000).
4. Bottini et al., "Cytotoxic and antiproliferative activity of the single agent epirubicin versus epirubicin plus tamoxifen as primary chemotherapy in human breast cancer: a single-institution phase III trial, "*Endocrine-Related Cancer*, 12: 383-392 (2005).
5. Bui et al., "Prognostic value of carbonic anhydrase IX and K67 as predictors of survival for renal clear cell carcinoma," *Journal of Urology*, 171: 2461-2466 (2004).
6. Chia and Yorida, "Carbonic anhydrase IX (CaIX) is an independent poor prognostic factor in early stage breast cancer: results from a large population-based tissue microarray (TMA) series," *Proceedings of the 27th San Antonio Breast Cancer Symposium*, Abstract 3015 (2004).
7. Chia et al., "Prognostic significance of a novel hypoxia-regulated marker, carbonic anhydrase IX, in invasive breast carcinoma," *Journal of Clinical Oncology*, 19: 3660-3668 (2001).
8. Christianson and Cox, "Catalysis by metal-activated hydroxide in zinc and manganese metalloenzymes," *Annual Reviews in Biochemistry*, 68: 33-57 (1999).
9. Colpaert et al., "The presence of a fibrotic focus in invasive breast carcinoma correlates with the expression of carbonic anhydrase IX and is a marker of hypoxia and poor prognosis," *Breast Cancer Research and Treatment*, 81: 137-147 (2003).
10. Cooper et al., "Intermittent hypoxia induces proteasome-dependent down-regulation of estrogen receptor alpha in human breast carcinoma," *Clinical Cancer Research*, 10: 8720-8727 (2004).
11. Coradini et al., "Hypoxia and estrogen receptor profile influence the responsiveness of human breast cancer cells to estradiol and antiestrogens," *Cellular and Molecular Life Sciences*, 61: 76-82 (2004).
12. Dowsett et al., "Response to specific antioestrogen (ICI182780) in tamoxifen-resistant breast cancer," *Lancet*, 345: 525 (1995).
13. Elston and Ellis, "Pathological prognostic factors in breast cancer. I. The value of histological grade in breast cancer: experience from a large study with long-term follow-up," *Histopathology* 19: 403-410 (1991).
14. Gerweck and Seetharaman, "Cellular pH gradient in tumor versus normal tissue: potential exploitation for the treatment of cancer," *Cancer Research*, 56: 1194-1198 (1996).
15. Gillies and Deamer, "Intracellular pH: methods and applications," *Current Topics in Bioenergetics*, 9: 63-87 (1978).
16. Harris, A. L., "Hypoxia—a key regulatory factor in tumour growth," *Nature Reviews Cancer*, 2: 38-47 (2002).
17. Höckel and Vaupel, "Tumor hypoxia: definitions and current clinical, biologic, and molecular aspects," *Journal of the National Cancer Institute*, 93: 266-276 (2001).
18. Höckel et al., "Association between tumor hypoxia and malignant progression in advanced cancer of the uterine cervix," *Cancer Research*, 56: 4509-4515 (1996).
19. Hui et al., "Coexpression of hypoxia-inducible factors 1alpha and 2alpha, carbonic anhydrase IX, and vascular endothelial growth factor in nasopharyngeal carcinoma and relationship to survival," *Clinical Cancer Research*, 8: 2595-2604 (2002).
20. Hussain et al., "Carbonic anhydrase IX, a marker of hypoxia: correlation with clinical outcome in transitional cell carcinoma of the bladder," *Oncology Reports*, 11: 1005-1010 (2004).
21. Kaluzova et al., "DNA damage is a prerequisite for p53-mediated proteasomal degradation of HIF-1alpha in hypoxic cells and down-regulation of the hypoxia marker carbonic anhydrase IX," *Molecular and Cellular Biology*, 24: 5757-5766 (2004).
22. Koukourakis et al., "Hypoxia-regulated carbonic anhydrase-9 (CA9) relates to poor vascularization and resistance of squamous cell head and neck cancer to chemoradiotherapy," *Clinical Cancer Research*, 7: 3399-3403 (2001).
23. Leek et al., "Necrosis correlates with high vascular density and focal macrophage infiltration in invasive carcinoma of the breast," *British Journal of Cancer*, 79: 991-995 (1999).
24. Loncaster et al., "Carbonic anhydrase (CA IX) expression, a potential new intrinsic marker of hypoxia: correlations with tumor oxygen measurements and prognosis in locally advanced carcinoma of the cervix," *Cancer Research*, 61: 6394-6399 (2001).
25. Lyman et al., "Impact of a 21-gene RT-PCR assay on treatment decisions in early-stage breast cancer," *Cancer*, 109(6): 1011-1018 (2007).
26. McCarty et al., "Estrogen receptor analyses. Correlation of biochemical and immunohistochemical methods using monoclonal antireceptor antibodies," *Archives in Pathology and Laboratory Medicine*, 109: 716-721 (1985).
27. Pastorekova et al., "A novel quasi-viral agent, MaTu, is a two-component system," *Virology*, 187: 620-626 (1992).
28. Potter and Harris, "Diagnostic, prognostic and therapeutic implications of carbonic anhydrases in cancer," *British Journal of Cancer*, 89: 2-7 (2003).
29. Raghunand and Gillies, "pH and chemotherapy," *Novartis Foundation Symposium*, 240: 199-211 (discussion 265-268) (2001).
30. Raghunand et al., "Enhancement of chemotherapy by manipulation of tumour pH," *British Journal of Cancer*, 80: 1005-1011 (1999).
31. Roos, A., "Weak acids, weak bases and intracellular pH," *Respiratory Physiology*, 33: 27-30 (1978).
32. Schmid et al., "HIF-1 and p53: communication of transcription factors under hypoxia," *Journal of Cellular and Molecular Medicine*, 8: 423-431 (2004).
33. Span et al., "Carbonic anhydrase-9 expression levels and prognosis in human breast cancer: association with treatment outcome," *British Journal of Cancer*, 89: 271-276 (2003).
34. Supuran et al., "Designing of novel carbonic anhydrase inhibitors and activators," *Current Medicinal Chemistry Cardiovascular and Hematological Agents*, 2: 51-70 (2004).
35. Svastova et al., "Hypoxia activates the capacity of tumor-associated carbonic anhydrase IX to acidify extracellular pH," *FEBS Letters*, 577: 439-445 (2004).
36. Swinson et al., "Carbonic anhydrase IX expression, a novel surrogate marker of tumor hypoxia, is associated with a poor prognosis in non-small-cell lung cancer," *Journal of Clinical Oncology*, 21: 473-482 (2003).
37. Wykoff et al., "Hypoxia-inducible expression of tumor-associated carbonic anhydrases," *Cancer Research*, 60: 7075-7083 (2000).
38. Zambetti et al., "Sequential adriamycin and CMF in metastatic breast cancer," *Oncologist*, 2: 223-227 (1997).

Abbreviations

The following abbreviations are used herein:

| | |
|---|---|
| aa | amino acid |
| ANOVA | analysis of variance |
| ATCC | American Type Culture Collection |
| bp | base pairs |
| CA | carbonic anhydrase |
| CAI | carbonic anhydrase inhibitor |
| $X^2$ | Chi-squared |
| Ci | curie |
| CI | confidence interval |
| cm | centimeter |
| CMF | regimen of cyclophosphamide (600 mg/m$^2$), methotrexate (40 mg/m$^2$), and 5-fluorouracil (600 mg/m$^2$) |
| CR | complete response |
| CS | cumulative survival |
| C-terminus | carboxyl-terminus |
| ° C. | degrees centigrade |
| DAB | diaminobenzidine tetrahydrochloride |
| DFS | disease-free survival |
| ds | double-stranded |
| EDTA | ethylenediaminetetraacetate |
| ELISA | enzyme-linked immunosorbent assay |
| EPI | epirubicin |
| ER | estrogen receptor |
| Gr | Grade |
| H&E | haepatoxylin and eosin |
| HR | hazard ratio |
| HRP | horseradish peroxidase |
| IC | intracellular |
| IFN | interferon (exemplary cytokine) |
| IL-2 | interleukin-2 (exemplary cytokine) |
| i.v. | intravenous |
| kb | kilobase |
| kbp | kilobase pairs |
| kd or kDa | kilodaltons |
| m | meter |
| M | molar |
| MAb | monoclonal antibody |
| min. | minute(s) |
| mg | milligram |
| ml | milliliter |
| mM | millimolar |
| mmol | millimole |
| n | number of cases |
| N | node status |
| ng | nanogram |
| nm | nanometer |
| nM | nanomolar |
| nt | nucleotide |
| N-terminus | amino terminus |
| OR | odds ratio |
| ORF | open reading frame |
| OS | overall survival |
| PBS | phosphate buffered saline |
| pCR | pathological complete response |
| PCR | polymerase chain reaction |
| PD | tumor progression |
| PG | proteoglycan |
| PgR | progesterone receptor |
| pHe | extracellular pH |
| pI | isoelectric point |
| PR | partial response |
| RCC | renal cell carcinoma |
| RT-PCR | reverse transcription polymerase chain reaction |
| SD | standard deviation |
| SDS | sodium dodecyl sulfate |
| SPSS | "Statistical Package for the Social Sciences" |
| SSPE | NaCl (0.18 M), sodium phosphate (0.01 M), EDTA (0.001 M) |
| Stg | stage |
| T | tumor stage |
| Tam/TAM | tamoxifen |
| TM | transmembrane |
| Tris | tris (hydroxymethyl) aminomethane |
| μCi | microcurie |
| μg | microgram |
| μl | microliter |
| μM | micromolar |

NUCLEOTIDE AND AMINO ACID SEQUENCE SYMBOLS

Figure 1A:
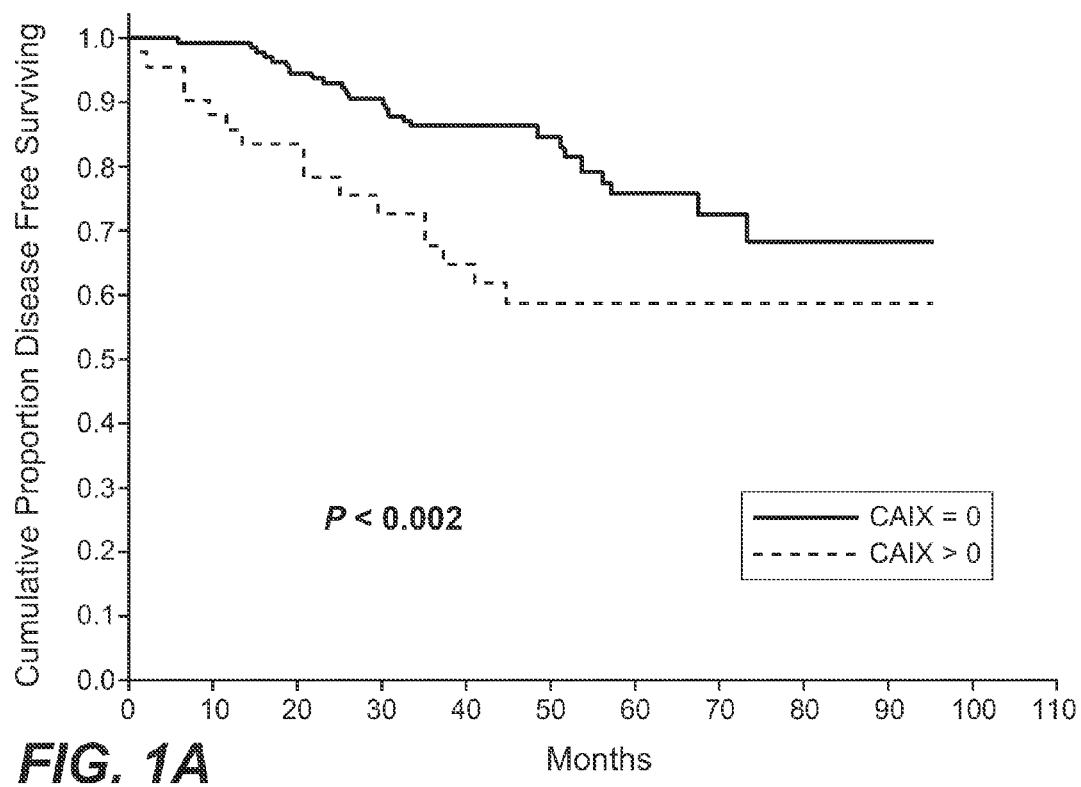
FIG. 1 graphically shows disease-free (A) and overall survival (B) of breast cancer patients according to CA IX status.
Figure 1B:
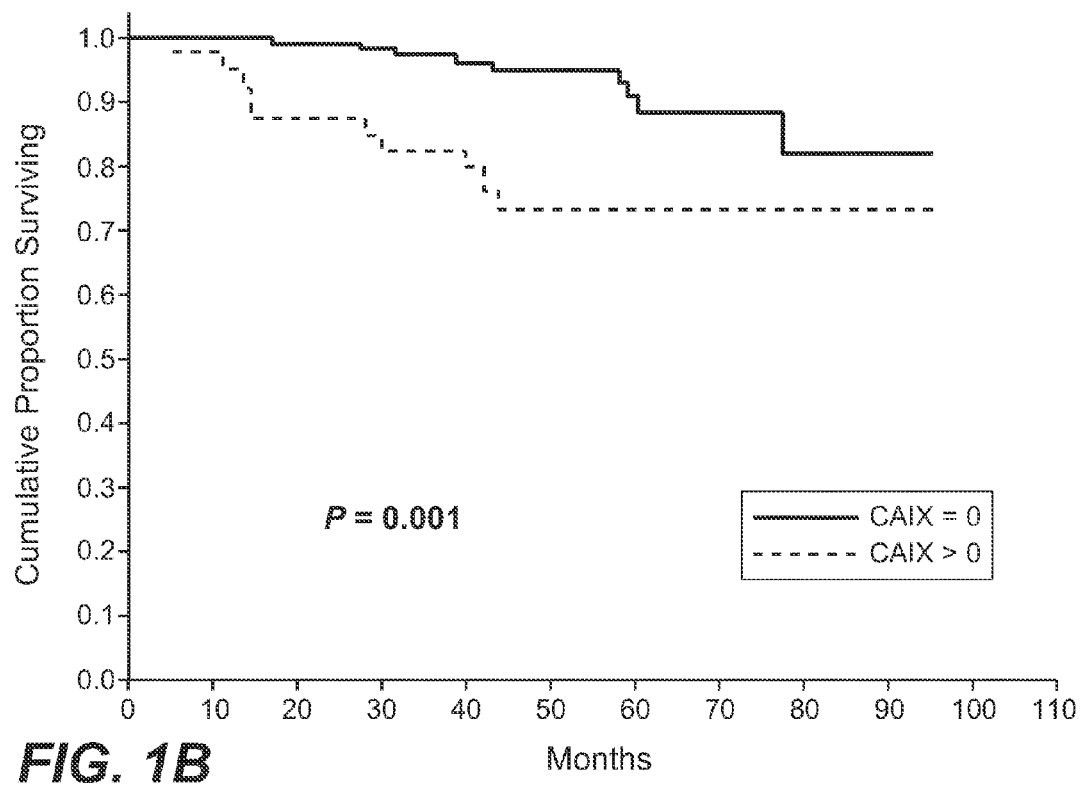

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention may be used herein to identify said amino acids as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

| Amino acid name | 3 Ltr. Abbrev. | 1 Ltr. Abbrev. |
|---|---|---|
| Threonine | Thr | T |
| Tryptophan | Trp | W |
| Tyrosine | Tyr | Y |
| Valine | Val | V |
| Unknown or other |  | X |

DETAILED DESCRIPTION

The invention provides methods for predicting resistance to endocrine therapy in a patient with an estrogen receptor (ER) positive breast tumor. The methods comprise detecting the presence, level, intensity and/or extent of MN/CA9 gene expression product, if any, in a sample taken from a patient that has been diagnosed with ER-positive breast cancer, particularly a patient being considered for, or undergoing, endocrine therapy. The MN/CA9 gene expression product can be MN/CA IX, a MN protein, a MN polypeptide, soluble MN/CA IX antigen (s-CA IX), MN/CA9 nucleic acids, particularly mRNA encoding MN/CA IX, a MN protein or a MN polypeptide, a cDNA corresponding to an mRNA encoding MN/CA IX, a MN protein or a MN polypeptide, or the like.

As used herein, "endocrine therapy" refers broadly to any therapy that is considered to modify (at least potentially) the effect of the endocrine environment to reduce growth of a preneoplastic/neoplastic cell or tumor. All endocrine treatment is systemic therapy, and may be medical (eg., through the use of drugs) or surgical (usually by ovariectomy). Types of endocrine therapies include antiestrogens, selective estrogen receptor modulators (SERMs), progesterone, antiprogesterone, estrogen or androgens, among other therapies. Exemplary endocrine therapies include raloxifene, steroidal and nonsteroidal aromatase inhibitors [e.g., Arimidex® (anastrozole); Femara® (letrozole)], and Faslodex® [fulvestrant; ICI 182,780; AstraZeneca]. Endocrine therapies targeting estrogen may inhibit or reduce the amount of estrogen available. For example, aromatase inhibitors prevent the conversion of androgen into estrogen, thereby reducing the amount of estrogen available. Estrogen receptor downregulators inhibit or reduce the number of estrogen receptors on the cell. As used herein, "antiestrogen" refers to those drugs that antagonize the estrogen receptor, such as tamoxifen, but does not include drugs that primarily act to lower estrogen levels in the body, such as aromatase inhibitors (AIs).

As used herein, "chemotherapy" refers to any chemical administered to kill, or inhibit the growth of, preneoplastic/neoplastic cells in a patient. Chemotherapy may comprise or consist of one or more alkylating agents, antimetabolites, anthracyclines, plant alkaloids, topoisomerase inhibitors, monoclonal antibodies, tyrosine kinase inhibitors, multikinase inhibitors, and alternative endocrine therapies (i.e., alternative to the endocrine therapy for which patient resistance is predicted).

In one embodiment of the invention, the MN/CA9 gene expression product levels are quantified in the ER-positive breast cancer patient sample, and said levels, including absence of MN/CA9 gene expression product, are correlated with a better or worse prognosis for the patient. Said MN/CA9 gene expression product is preferably MN/CA IX quantitated in a sample taken from the patient. The methods can be used, for example, to predict ER-positive breast cancer patient response to endocrine therapy, and to aid in the selection of therapies. In particular, elevated levels of MN/CA9 gene expression products (above levels found in normal breast cells) can be used to identify high risk ER-positive breast cancer patients in need of adjuvant therapies, particularly those in need of adjuvant therapies from the outset.

A preferred method of detecting, or detecting and quantitating MN/CA9 gene expression product in a patient sample is by immunohistochemical staining of MN/CA IX. More preferably, said MN/CA9 gene expression product detection is by immunohistochemical staining, and said quantitating comprises determining the percentage of immunoreactive cells, the intensity and/or extent of immunostaining of immunoreactive cells. Still more preferably, said detection comprises the use of a MN/CA IX-specific monoclonal antibody, preferably the M75 MAb secreted by the hybridoma VU-M75 which has Accession No. ATCC HB 11128 and has been deposited under the Budapest Treaty at the American Type Culture Collection. In one preferred embodiment of the invention, the immunostaining is quantified in carcinoma cells by semi-quantitative scoring as previously described [Colpaert et al. (2003)], in which a score of 0-2 is given for the intensity of staining (0, no staining; 1, weak staining; 2, moderate to strong staining), and for all comparisons with survival and response, wherein any staining is counted as positive.

In an alternative preferred embodiment, preferred assays to be used according to the methods of the invention in detecting and quantitating overexpression of said MN/CA9 gene expression product in breast cancer cells, are nucleic acid-based assays, wherein said MN/CA9 gene expression product comprises a mRNA encoding MN/CA IX, a MN protein or a MN polypeptide, or a cDNA complementary to mRNA encoding MN/CA IX, a MN protein or a MN polypeptide. Preferably, said detecting and quantitating are by in situ hybridization or by Northern blotting.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

It can be appreciated by those of skill in the art that various other preneoplastic/neoplastic samples can be used to quantify the MN/CA9 gene expression products. For example, in the case of a patient afflicted with a breast tumor, the sample may be taken from the tumor or from a metastatic lesion derived from the tumor, or from the extracellular fluid within or immediately surrounding the tumor or metastatic lesion.

Neoplastic Cells/Tissues

As used herein, "cancerous" and "neoplastic" have equivalent meanings, as well as "precancerous" and preneoplastic".

In a preferred embodiment of the invention, the MN/CA9 gene expression product is MN/CA IX antigen, and the MN/CA IX antigen is detected and quantitated in vertebrate samples, preferably mammalian samples, more preferably human samples, comprising preneoplastic/neoplastic cells, particularly, neoplastic cells. Such samples can be tissue specimens, tissue extracts, body fluids, cells, cell lysates and cell extracts, among other samples. Preferred tissue specimens to assay by immunohistochemical staining, for example, include cell smears, histological sections from biopsied tissues or organs, and imprint preparations among other tissue samples. An exemplary immunohistochemical staining protocol is described below in the *Materials and Methods* section (infra). Such tissue specimens can be variously maintained; for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, fine needle, percutaneous punch, and surface biopsies, among other biopsy techniques. Preferred tissue samples are formalin-fixed, paraffin-embedded tissue samples.

Tumor Stage and Grade

The TNM classification devised by the International Union Against Cancer (UICC) and accepted by the American Joint Commission on Cancer Staging is a world standard [Greene et al, eds. *American Joint Committee on Cancer (AJCC) Cancer Staging Manual.* 6th ed. New York: Springer-Verlag, (2002)]. The TNM is based on the clinical features of tumor (T), the regional lymph nodes (N), and the presence or absence of distant metastases (M). The tumor is characterized by its size, so that a T1 is a tumor less than 2 cm, a T2 is 2 to 5 cm, and a T3 is over 5 cm. Similarly, N0 represents negative, or normal, regional lymph nodes, and so on [see, e.g., Kufe et al. (eds.), *Cancer Medicine* 6, London: B. C. Decker, Inc., (2003), Section 31, Subsection 121].

Tumor grade indicates the degree of tumor differentiation. In general, a low grade indicates a well differentiated tumor, and a high grade indicates an undifferentiated tumor. In the Examples described below, the Nottingham system [Elston and Ellis (1991)] was used to determine tumor grade.

Other methods of determining tumor stage and grade are known in the art and could be adapted to be used according to the methods of the invention.

Assays

According to the methods of the instant invention, many assays can be used to determine MN/CA9 gene overexpression in a sample taken from a breast cancer patient. Many formats can be adapted for use with the methods of the present invention. For example, the detection and quantitation of MN/CA IX can be performed by Western blots, enzyme-linked immunosorbent assays, radioimmunoassays, competition immunoassays, dual antibody sandwich assays, immunohistochemical staining assays, agglutination assays, fluorescent immunoassays, immunoelectron and scanning microscopy using immunogold, among other assays commonly known in the art. The quantitation of MN/CA9 gene expression products in such assays can be adapted by conventional methods known in the art; for example, if the detection method is by immunohistochemical staining, the determination of MN/CA IX overexpression can be performed by determining the percentage of immunoreactive cells and/or the intensity or extent of immunostaining of immunoreactive cells, and can additionally comprise addition or multiplication of these values, or other mathematical calculations using these values.

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label according to this invention is the method of labeling the antibodies using peroxidase. Also preferred is $^{125}$I, and a preferred method of labeling the antibodies is by using chloramine-T [Dalbadie-McFarland et al., *PNAS* (USA), 79(21): 6409-6413 (November 1982)]. Many other means of visualizing the MN/CA9 gene expression products known to those of skill in the art can also be used.

It can further be appreciated that alternate methods, in addition to those disclosed herein, can be used to detect and quantify the MN/CA9 gene expression products. For example, immunological assays for detecting, or detecting and quantitating, s-CA IX overexpression in human body fluid samples are described in Pastorek et al., US Patent Application No. US2005031623 A1, and Zavada et al., *Br J Cancer,* 89(6): 1067-71 (2003). Body fluids which can be assayed for the presence of s-CA IX can include any of the following: blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchioalveolar lavages and cerebrospinal fluid, among other fluids. It is preferred that the MN antigen be concentrated from a larger volume of body fluid before testing. A preferred body fluid to assay for breast cancer would be breast exudate or serum.

Exemplary Immunohistochemical Assays

An exemplary semiquantitative immunohistochemical assay described in Example 1 below uses antibody staining to investigate the expression of MN/CA IX. Two core tissue biopsies are taken from the paraffin-embedded tissue section of an ER-positive breast cancer patient, and stained with the MN/CA IX-specific monoclonal antibody M75. The sections are then reacted with a secondary rabbit anti-mouse antibody labeled with HRP (horseradish peroxidase). The immunoperoxidase complexes are then visualized with a chromogen, such as diaminobenzidine tetrahydrochloride (DAB) or 3-amino-9-ethyl carbazole (AEC). The immunostaining of breast cancer patient samples was quantified by semi-quantitative scoring as previously described (Colpaert et al. 2003).

Nucleic Acid-Based Assays

In certain embodiments of the invention, overexpression of mRNA or cDNA that encodes MN/CA IX, a MN protein or a MN polypeptide is detected and correlated with a prediction of endocrine therapy resistance, preferably tamoxifen resistance, and/or prognosis for an ER-positive breast cancer patient. Nucleic acid-based assays for detecting, or detecting and quantitating, MN/CA9 gene overexpression in vertebrate samples are described in greater detail elsewhere, for example, in Zavada et al., U.S. Pat. No. 7,186,514. An exemplary nucleic acid-based method is Northern blotting, where the nucleic acid sequence used as a probe for detecting MN/CA9-specific mRNA expression is complementary to all or part of the MN/CA9 cDNA sequence. A preparation of RNA is run on a denaturing agarose gel, and transferred to a suitable support, such as activated cellulose, nitrocellulose or glass or nylon membranes. The nucleic acids used to detect the MN/CA9 mRNA or cDNA may be radiolabelled and analyzed by autoradiography. Non-radioactive labels, for example, such as fluorophores or reporter groups such as digoxigenin may also be used to detect the MN/CA9 mRNA or cDNA.

An alternate preferred method for measuring MN-specific mRNA expression is the detection of CA9 mRNA expression via hybridization of a nucleic acid probe derived from MN/CA9 cDNA sequence to RT-PCR products generated from RNA isolated from a biological sample. Exemplary PCR primers designed to amplify a 240 bp cDNA fragment of the CA9 gene are sense 5'-AGGAGGATCTGCC CAGTGA-3' [SEQ ID NO: 11]; antisense 5'-GCCAATGACTCTGGT-CATC-3') [SEQ ID NO: 12]. Murakami et al. and Uemura et al. have reported that MN detection by RT-PCR in renal cell carcinoma (RCC) patient samples correlate well with immunohistochemistry [Murakami et al., *BJU Int.,* 83: 743-747 (1999); Uemura et al., *Br. J. Cancer,* 81: 741-746 (1999)].

According to the methods of the invention, the MN/CA9 mRNA or cDNA that is detected in the nucleic-acid based assays represents nucleic acid sequences that are unique to the MN gene. Said MN/CA9 mRNA or cDNA that is detected in the nucleic-acid based assays is preferably at least 16 nucleotides in length, but may be considerably longer. Preferably, said MN/CA9 mRNA (or cDNA) encodes (or hybridizes under stringent hybridization conditions to nucleic acids that encode) MN proteins or polypeptides that are specifically bound by monoclonal antibodies designated M75 that are produced by the hybridoma VU-M75 deposited at the American Type Culture Collection (ATCC) at 10801 University Blvd., Manassas, Va. 20110-2209 (USA) under ATCC No. HB 11128, and/or by monoclonal antibodies designated V/10 produced by the hybridoma V/10-VU deposited at the International Depository Authority (IDA) of the Belgian Coordinated Collections of Microorganisms (BCCM) at the Laboratorium voor Moleculaire Blologie-Plasmidencollectie (LMPB) at the Universeit Gent, K. L. Ledeganckstraat 35, B-9000 Gent, Belgium [BCCM/LMBP] under the Accession No. LMBP 6009CB.

MN Gene and Protein

The terms "MN/CA IX" and "MN/CA9" are herein considered to be synonyms for MN. Also, the G250 antigen is considered to refer to MN protein/polypeptide [Uemura et al., *J. Urol.* 157 (4 Suppl.): 377 (Abstract 1475; 1997)].

Zavada et al., WO 93/18152 and/or WO 95/34650 disclose the MN cDNA sequence [SEQ ID NO: 1], the MN amino acid sequence [SEQ ID NO: 2], and the MN genomic sequence [SEQ ID NO: 3]. The MN gene is organized into 11 exons and 10 introns.

The ORF of the MN cDNA [SEQ ID NO: 1] has the coding capacity for a 459 amino acid protein with a calculated molecular weight of 49.7 kd. The overall amino acid composition of MN/CA IX is rather acidic, and predicted to have a pI of 4.3. Analysis of native MN/CA IX from CGL3 cells by two-dimensional electrophoresis followed by immunoblotting has shown that in agreement with computer prediction, MN/CA IX is an acidic protein existing in several isoelectric forms with pIs ranging from 4.7 to 6.3. [CGL3 cells are hybrid HeLa fibroblast cells that are tumorigenic, derived from HeLa D98/AH.2 (also known as HeLa S), a mutant HeLa clone that is hypoxanthine guanine phosphoribosyl transferase-deficient (HGPRT⁻) reported in Stanbridge et al., *Science,* 215: 252-259 (15 Jan. 1982).]

The first thirty seven amino acids of MN/CA IX is the putative MN signal peptide [SEQ ID NO: 7]. MN/CA IX has an extracellular domain [amino acids (aa) 38-414; SEQ ID NO: 8], a transmembrane domain [aa 415-434; SEQ ID NO: 9] and an intracellular domain [aa 435-459; SEQ ID NO: 10]. The extracellular domain contains the proteoglycan-like domain [aa 53-111: SEQ ID NO: 5] and the carbonic anhydrase (CA) domain [aa 135-391; SEQ ID NO: 6].

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

MN Proteins and Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence represented by SEQ ID NO: 2. Preferred MN proteins/polypeptides are those proteins and/or polypeptides that have substantial homology with the MN protein [SEQ ID NO: 2]. For example, such substantially homologous MN proteins/polypeptides are those that are reactive with MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

As used herein, "MNCA IX positivity" or "presence of MN/CA9 gene expression product" refers to a determination that the cells in a preneoplastic/neoplastic sample taken from an ER-positive breast cancer patient overexpress the MN/CA9 gene. Correspondingly, "MN/CA IX negativity" or "absence of MN/CA9 gene expression product" refers to a determination that cells in a preneoplastic/neoplastic sample taken from an ER-positive breast cancer patient do not overexpress the MN/CA9 gene.

It can be appreciated that a protein or polypeptide produced by a preneoplastic/neoplastic cell in vivo could be altered in sequence from that produced by a tumor cell in cell culture or by a transfected cell. Thus, MN proteins and/or polypeptides which have varying amino acid sequences including without limitation, amino acid substitutions, extensions, deletions, truncations, interpolations and combinations thereof, fall within the contemplated scope of this invention, provided the protein or polypeptide containing them is immunogenic, and antibodies elicited by such a polypeptide or protein cross-react with naturally occurring MN proteins and polypeptides to a sufficient extent to provide protective immunity and/or anti-tumorigenic activity when administered as a vaccine. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

Nucleic Acid Probes

Nucleic acid probes of this invention are those comprising sequences that are complementary or substantially complementary to the MN cDNA sequence [SEQ ID NO: 1] or to other MN gene sequences, such as, the complete genomic sequence [SEQ ID NO: 3]. The phrase "substantially complementary" is defined herein to have the meaning as it is well understood in the art and, thus, used in the context of standard hybridization conditions. The stringency of hybridization conditions can be adjusted to control the precision of complementarity. Two nucleic acids are, for example, substantially complementary to each other, if they hybridize to each other under stringent hybridization conditions.

Stringent Hybridization Conditions

Stringent hybridization conditions are considered herein to conform to standard hybridization conditions understood in the art to be stringent. Only very closely related nt sequences having a homology of at least 80-90%, preferably at least 90%, would hybridize to each other under stringent hybridization conditions.

For example, it is generally understood that stringent conditions encompass relatively low salt and/or high temperature conditions, such as provided by 0.02 M to 0.15 M NaCl at temperatures of 50° C. to 70° C. such as, 0.15 M to 0.9 M salt at temperatures ranging from 20° C. to 55° C. Less stringent conditions can be made more stringent by adding increasing amounts of formamide, which serves to destabilize hybrid duplexes as does increased temperature, such as provided by 0.15 M to 0.9 M NaCl in the presence of 50% formamide at 42° C. with a final wash of 0.1% SSPE and 0.1% SDS at 65° C.

Exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery, Oral Medicine, Oral Pathology*. 71(6): 721-725 (June 1991); and in U.S. Pat. No. 5,989,838, U.S. Pat. No. 5,972,353, U.S. Pat. No. 5,981,711, and U.S. Pat. No. 6,051,226.

Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen.

Antibodies useful according to the methods of the invention may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies [Glennie et al., *Nature*, 295: 712-714 (1982)]. Fab proteins including Fab' and F(ab)$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of the $V_H$ and $V_L$ regions]; Fc proteins; "hybrid" antibodies capable of binding more than one antigen; constant-variable region chimeras; "composite" immunoglobulins with heavy and light chains of different origins; bispecific antibodies, preferably bispecific MAbs; "altered" antibodies with improved specificity and other characteristics as prepared by standard recombinant techniques and also oligonucleotide-directed mutagenesis techniques [Dalbadie-McFarland et al., *PNAS* (USA), 79(21): 6409-6413 (1982)]. Particularly preferred antibodies, particularly for therapeutic use, are humanized, preferably fully humanized antibodies, preferably fully humanized MN/CA IX-specific monoclonal antibodies or biologically active fragments thereof.

The antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label according to this invention is $^{125}$I, and a preferred method of labeling the antibodies is by using chloramine-T [Hunter, W. M., "Radioimmunoassay," *In: Handbook of Experimental Immunology*, pp. 14.1-14.40 (D. W. Weir ed.; Blackwell, Oxford/London/Edinburgh/Melbourne; 1978)].

Representative monoclonal antibodies useful according to this invention include Mabs M75, MN9, MN12 and MN7 described in earlier Zavada et al. patents and patent applications. [U.S. Pat. No. 6,297,041; U.S. Pat. No. 6,204,370; U.S. Pat. No. 6,093,548; U.S. Pat. No. 6,051,226; U.S. Pat. No. 6,004,535; U.S. Pat. No. 5,989,838; U.S. Pat. No. 5,981,711; U.S. Pat. No. 5,972,353; U.S. Pat. No. 5,955,075; U.S. Pat. No. 5,387,676; US App. Nos: 20030049828 and 20020137910; and Int'l. Pub. No. WO 03/100029]. Monoclonal antibodies useful according to this invention serve to identify MN proteins/polypeptides in various laboratory diagnostic/prognostic tests, for example, in clinical samples. For example, monoclonal antibody M75 (Mab M75) is produced by mouse lymphocytic hybridoma VU-M75, which was deposited under ATCC designation HB 11128 on Sep. 17, 1992 at the American Tissue Type Culture Collection [ATCC]. The production of hybridoma VU-M75 is described in Zavada et al., International Publication No. WO 93/18152. Mab M75 recognizes both the nonglycosylated GST-MN fusion protein and native MN protein as expressed in CGL3 cells equally well. The M75 Mab recognizes both native and denatured forms of MN protein [Pastorekova et al., *Virology*, 187: 620-626 (1992)].

General texts describing additional molecular biological techniques useful herein, including the preparation of antibodies include Berger and Kimmel, *Guide to Molecular Cloning Techniques, Methods in Enzymology*, Vol. 152, Academic Press, Inc., Sambrook et al., *Molecular Cloning: A Laboratory Manual*, (Second Edition, Cold Spring Harbor Laboratory Press; Cold Spring Harbor, N.Y.; 1989) Vol. 1-3; *Current Protocols in Molecular Biology*, F. M. Ausabel et al. [Eds.], Current Protocols, a joint venture between Green Publishing Associates, Inc. and John Wiley & Sons, Inc. (supplemented through 2000), Harlow et al., *Monoclonal Antibodies: A Laboratory Manual*, Cold Spring Harbor Laboratory Press (1988), Paul [Ed.]; *Fundamental Immunology*, Lippincott Williams & Wilkins (1998), and Harlow et al., *Using Antibodies: A Laboratory Manual*, Cold Spring Harbor Laboratory Press (1998).

MN/CA IX and Prognosis: Use in Breast Cancer Therapy Selection

As MN/CA IX positive staining correlated with worse outcome and tamoxifen resistance (Example 1), detection and quantitation of CA IX can be used to identify high-risk patients in need of therapies other than tamoxifen, or in need of adjuvant therapies, including adjuvant chemotherapy and MN-targeted therapies. Careful patient selection and stratification to various adjuvant therapies may delineate those patients most likely to respond to treatment. For example, resistance to tamoxifen does not necessarily imply resistance to other endocrine therapies, including other antiestrogens. Conventional treatment options for women who are resistant to tamoxifen may include discontinuation of tamoxifen, an alternative endocrine therapy, or systemic chemotherapy; however, resistance to tamoxifen does not necessarily indicate against the use of tamoxifen, if clinical factors indicate that its continued use may have some benefit. Similarly, therapies based on monoclonal antibodies to CA IX or immunotherapy with CA IX-based vaccine, or CA9-directed gene therapies can also be considered according to CA IX detection and quantitation.

Selection of Additional/Alternative Therapies

In one aspect of the invention, the presence of MN/CA9 gene expression product in a sample from a breast cancer patient with an ER-positive tumor is indicative of probable resistance to endocrine therapy, particularly antiestrogen therapy, more particularly tamoxifen, and of selection and administration of additional or alternative therapies. Such additional or alternative therapies may comprise adjuvant chemotherapy, alternative endocrine therapy, MN-targeted therapy, and therapies targeting additional oncogenes or oncoproteins, preferably oncoproteins such as Her-2 whose overexpression has been correlated with MN/CA9 overexpression. In general, if a tumor appears to be rapidly progressing, adjuvant non-endocrine chemotherapy would be preferred over alternative endocrine therapy. A finding of probable resistance to an endocrine therapy, particularly tamoxifen, may still indicate that there can be a clinical benefit to administering that therapy, depending upon clinically approved protocols. For example, tamoxifen may still be administered to breast cancer patients that have ER-positive, MN-positive tumors. However, the finding of an ER-positive, MN-positive tumor in a breast cancer patient is an indication that the patient should be treated more aggressively (with additional therapy or therapies) from the outset.

In view of a prediction of probable resistance to antiestrogens, patient therapy selection will depend upon many additional factors, such as a woman's menopausal status, and the grade, progress, and stage of the breast cancer (e.g., low or high grade, rapid or slow progression, early stage or metastatic). In general, however, the presence of MN/CA9 gene expression in an ER-positive breast cancer patient sample would point to selection of an additional/alternate therapy, preferably in certain cases, those unaffected by low pH, as MN/CA9 is associated with acidification of the extracellular environment.

The mechanism for the correlation of CA IX positivity and tamoxifen resistance in ER-positive breast cancer is not clearly understood. For example, one fairly probable underlying mechanism is that wherein CA IX is a marker for biochemical pathways that bypass the estrogen receptor. Under that understanding, the presence of CA IX in a tumor derived from an ER-positive breast cancer patient would be considered to indicate that the patient would be resistant to endocrine therapies in general, and other therapeutic options may be preferably indicated instead (nonendocrine chemotherapies such as, e.g., taxols and MN-targeted therapies, among others). However, it could be that CA IX is acting more predominantly as a marker of acidic inhibition of tamoxifen uptake, under which understanding it would be considered likely that other endocrine therapies could be used with clinical benefit.

I. Additional/Alternative Chemotherapy

In the case of CA IX-positive expression and consequent prediction of probable resistance to endocrine treatment, particularly tamoxifen resistance, in ER-positive breast cancer, additional/alternative therapies that can be considered include adjuvant chemotherapy. Preferred adjuvant chemotherapy would comprise a taxane, preferably paclitaxel [Taxol™], protein-bound paclitaxel [Abraxane™] or docetaxel [Taxotere]. Other adjuvant chemotherapy that can be considered for use includes Gemcitabine [Gemzar™; Eli Lilly and Co.], a nucleoside analog; vinorelbine [Navelbine™]; capecitabine [Xeloda™], ixabepilone [Ixempra™], mitoxantrone [Novantrone™]; and leucovorin. Depending on the clinical context, in certain cases the anthracyclines epirubicin and doxorubicin would be preferably used. Other preferred chemotherapy based on the presence of CA IX in breast tumors would comprise prodrugs that are activated by hypoxia.

On the other hand, in certain cases depending on clinical factors, weakly basic chemotherapeutic agents would not be preferred alternative chemotherapy for CA IX-expressing ER-positive breast cancers. Such weakly basic chemotherapeutic agents prescribed for breast cancer include, for example, the vinca alkaloids. Vinca alkaloids (VAs) such as vincristine, vinblastine, vindesine and vinorelbine are antineoplastic drugs that inhibit tubulin polymerisation into microtubules, induce mitotic G2/M arrest, activate c-Jun N-terminal kinase (JNK) and induce apoptosis. [Martinez-Campa et al., *Breast Cancer Res Treat.*, 98(1): 81-9 (2006).] However, therapy selection requires balancing many considerations. For example, although anthracyclines have been reported as having reduced cellular uptake and toxicity to MCF-7 cells at pH 6.8 compared to pH 7.4 [Raghunand et al. (1999)], it may still be desirable to use an anthracycline, because there may be beneficial effects of an anthracycline used in combination with other drugs that overcome any inhibitory effects caused by acid conditions.

II. Alternative/Additional Endocrine Therapy

Based on CA IX overexpression in an ER-positive breast cancer patient sample, the choice of an alternative/additional endocrine therapy depends in large part upon whether the ER-positive breast cancer patient is premenopausal or postmenopausal. Such preferred alternative/additional endocrine therapy may comprise therapy selected from any of the following therapies, or combinations thereof: antiestrogens, preferably other than tamoxifen, such as fulvestrant [Faslodex®], estrogen deprivation therapies, including gonadotropin releasing hormone agonists [GnRH], such as goserelin [Zoladex®] or leuprolide [Lupron®]; sex steroid hormones (progestins, androgens, and/or estrogen); and ovariectomy.

III. MN-Targeted Therapies

Because of MN's unique characteristics, it is an attractive candidate target for cancer therapy. In comparison to other tumor-related molecules (e.g. growth factors and their receptors), MN has the unique property of being differentially expressed in preneoplastic/neoplastic and normal tissues. Because of the extremely limited expression of MN protein in normal tissues, chemotherapeutic agents that target its expression would be expected to have reduced side effects, relative to agents that target proteins more extensively found in normal tissues (e.g., tamoxifen which binds the estrogen receptor). Furthermore, Phase I and II clinical trials of an MN-specific drug, Rencarex®, have shown that at least one MN-specific agent is well-tolerated, with no serious drug-related side effects, further supporting MN as a possible target for cancer chemotherapy.

Many MN-directed therapies may be useful according to the methods of the present invention, alone or in combination with other therapies to treat ER-positive breast cancers associated with abnormal MN expression. As used herein, "MN-targeted therapy" refers to either CA9-targeted therapy and CA IX-targeted therapy, or both; that is, any therapy targeting either CA9 nucleic acids or MN protein. Preferred therapies comprise therapies selected from the group consisting of MN-specific antibodies, MN-specific carbonic anhydrase inhibitors, MN antisense therapies, MN RNA interference, and MN gene therapy vectors; some of which preferred therapies are described in greater detail below. The therapeutic use of MN-specific anti-idiotype antibodies and MN gene therapy vectors is described in greater detail elsewhere, for example, in Soyupak and Erdogan, US Patent Application No. 20070224606 A1, which reference is hereby incorporated by reference.

MN-Specific Antibodies: The MN-specific antibodies, monoclonal and/or polyclonal, preferably monoclonal, may be used therapeutically in the treatment of CA9-expressing breast cancer, either alone or in combination with chemotherapeutic drugs or toxic agents, such as ricin A. Further preferred for therapeutic use would be biologically active antibody fragments. Also preferred MN-specific antibodies for such therapeutic uses would be MN-specific humanized monoclonal antibodies, fully human monoclonal antibodies, and/or bispecific antibodies.

MN-specific antibodies can be administered in a therapeutically effective amount, preferably dispersed in a physiologically acceptable, nontoxic liquid vehicle, to patients afflicted with breast cancer expressing MN/CA IX. The MN-specific antibody can be given alone or as a carrier of an anti-tumor drug. Among the various antiproliferative, antineoplastic or cytotoxic agents that may be linked to the MN-specific antibodies are antimetabolites, such as the antifolate, methotrexate, or the purine or pyrimidine analogs mercaptopurine and fluorouracil. Others include antibiotics, lectins such as ricin and abrin, toxins such as the subunit of diphtheria toxin, radionuclides such as $^{211}$Astatine and $^{131}$Iodine, radiosensitizers such as misanidazole or neutron sensitizers such as boron containing organics. Such agents may be attached to the antibody by conventional techniques such as glutaraldehyde cross-linking.

MN-specific antibodies can be used to target cytotoxic cells (e.g. human T cells, monocytes or NK cells). Cytotoxic cells can be attached to MN-expressing tumor cells through Fc receptors on the cytotoxic cells, which bind the Fc portion of a MN-specific antibody, or via a bridging antibody of dual specificity, that is, a bispecific antibody specific for MN protein and for the cytotoxic cell.

The cytotoxic cell can be targeted by allowing the bispecific antibody to bind the cell. After targeting, the cells can be administered to the patient. Therapy with targeted cells can be used as an adjunct to surgical therapy, radiation therapy, or chemotherapy.

MN-Specific Carbonic Anhydrase Inhibitors

The novel methods of the present invention comprise inhibiting the growth of preneoplastic/neoplastic cells with compounds that preferentially inhibit the enzymatic activity of MN protein. Said compounds are organic or inorganic, preferably organic, more preferably sulfonamides. More preferably, said compounds are aromatic or heterocyclic sulfonamides, or pyridinium derivatives of aromatic or heterocyclic sulfonamides. These preferred pyridinium derivatives of sulfonamides are likely to have fewer side effects than other compounds in three respects: they are small molecules, they are membrane-impermeant, and they are specific potent inhibitors of the enzymatic activity of the tumor-associated MN protein. The pyridinium derivatives of sulfonamides useful according to the present invention can be formed, for example, by creating bonds between pyrylium salts and aromatic or heterocyclic sulfonamide reagents, as described in U.S. Patent Application No. 2004/0146955, which is hereby incorporated by reference. The aromatic or heterocyclic sulfonamide portion of a pyridinium salt of a sulfonamide compound can be called the "head," and the pyridinium portion can be called the "tail."

It can be appreciated by those of skill in the art that various other MN-preferential sulfonamide carbonic anhydrase inhibitors can be useful according to the present invention.

IV. Therapies Targeting Additional Oncogenes

Additional or alternative therapies that may be selected on the basis of MN/CA9 overexpression in an ER-positive breast cancer patient, are therapies targeting oncogenes found to be co-expressed with MN/CA9 in breast cancer, such as c-erbB-2/HER-2. As reported in Bartosova et al., (2002) and in Example 1 below, a significant correlation of expression of the two genes has been observed in breast cancer patients. Trastuzumab or Herceptin® is a humanized mab to HER-2 used to treat HER-2-positive cancers, particularly breast cancers, more particularly metastastic breast cancer [Horton, M. B., *Cancer Control*, 9(6): 499-507 (2002)]. Herceptin® can be given alone to a patient but can enhance the effectiveness of several chemotherapeutic agents. It would be advantageous to test ER-positive breast cancer patients for both HER-2 and MN/CA IX expression to enlarge the clinical perspective, therapeutic resources and diagnostic/prognostic parameters to pick the optimal therapeutic combinations for the most promising treatment outcomes.

Diagnostic/Prognostic Imaging

Positron emission tomography [PET] imaging in assessment of endocrine tumors has been until recently restricted to the use of $^{18}$F-fluoro-deoxy-D-glucose (18F-FDG). Being a marker of metabologically active lesions that show high grading and low differentiation, FDG is not ideal for this purpose since the majority of endocrine tumors are slow growing and highly differentiated [Khan et al., *Minerva Endocrinol.*, Feb. 15, 2008 Epub ahead of print].

For the diagnostic/prognostic imaging methods of the invention, wherein MN/CA IX presence is detected and used to indicate resistance to endocrine therapy, preferably resistance to antiestrogen therapy, the methods preferably comprise the use of labeled MN/CA IX-specific antibodies or labeled MN/CA IX-specific inhibitors, such as MN/CA IX-specific aromatic or heterocyclic sulfonamides. A preferred imaging method is PET imaging, and a preferred tracer for PET imaging purposes using MN/CA IX-specific inhibitors is the fluorine isotope $^{18}$F, which may be incorporated, for example, in a $CF_3$ moiety.

Computerized MN/CA IX Data Analysis

The correlation of MN/CA9 expression (for example, level and/or extent) and breast cancer prognosis can be analyzed by any number of methods known to one of skill in the art, for example, by computer program. Such a computer program could comprise algorithms for correlating CA9 expression data derived from a breast cancer patient with a probable prognosis.

The following examples are for purposes of illustration only and are not meant to limit the invention in any way.

MATERIALS AND METHODS

In Examples 1-6 (infra), MN/CA IX expression was evaluated in a series of breast cancer specimens obtained before and after primary anthracycline and tamoxifen therapy from breast cancer patients enrolled in a randomized trial of primary therapy, with the aim to: (1) assess the relationship between MN/CA IX expression and disease-free survival (DFS), (2) evaluate expression in relation to response to the therapy with a single cytotoxic agent, where acid pH could contribute to drug resistance, and (3) assess changes in MN/CA IX expression after treatment and their relation to the outcome.

Patients: Patients with T2-4 N0-1 breast cancer [TNM staging system] were recruited in a randomized trial comparing single agent epirubicin (EPI arm) versus epirubicin+tamoxifen (EPI-Tam arm) as primary systemic treatment. The results of this trial have recently been published [Bottini et al., (2005)]. Two hundred and eleven patients were enrolled in which one hundred and five were randomized to receive epirubicin alone and one hundred and six were randomized to receive epirubicin+tamoxifen. In first presentation, an incision biopsy was performed on each patient and a small tissue sample (0.5-0.8 cm) was removed. Chemotherapy was started within 2 days of diagnosis. Patients in the EPI arm received 60 mg/m$^2$ epirubicin (Farmorubicine™, Pharmacia Italia S.p.A., Via Roberto Koch 1.2, 1-20100 Milan, Italy) by slow i.v. push on days 1 and 2, while patients in the EPI-TAM arm received 60 mg/m² epirubicin by slow i.v. push on days 1 and 2, and 30 mg tamoxifen (Kessar™, Pharmacia Italia S.p.A.) daily. Epirubicin injections were repeated every 21 days for four cycles before definitive surgery, whereas tamoxifen was given continuously until definitive surgery. Surgery was planned after complete clinical reassessment. Quadrantectomy or modified radical mastectomy was performed when indicated in association with complete axillary node dissection. All patients subjected to quadrantectomy underwent irradiation of the residual breast (60 Gy delivered over 6 weeks). All patients received four cycles of cyclophosphamide (600 mg/m²), methotrexate (40 mg/m²), and 5-fluorouracil (600 mg/m²) intravenously on days 1 and 8 every 28 days (CMF regimen) [Zambetti et al., (1997)] postoperatively. Patients with ER-positive primary tumor in both arms received tamoxifen (20 mg, i.e. lower than the primary dose) starting after surgery, up to progression or for a maximum of 5 years.

Treatment evaluation: Each month, the size of the primary tumor and axillary lymph nodes, when appreciable, were measured with a caliper by the same clinician. Response was assessed by the clinical measurement of the changes in the product of the two largest diameters recorded in two successive evaluations. According to the World Health Organization criteria, tumor progression (PD) was defined as an increase of at least 25% in tumor size; stable disease as an increase of less than 25%, or a reduction of less than 50%; partial response (PR) as a tumor shrinkage greater than 50%; and complete response (CR) as the complete disappearance of all clinical signs of the disease.

Pathological CR (pCR) was defined as the absence of neoplastic cells in the breast and in the axillary lymph nodes.

Histopathologic grade and immunohistochemistry: Tumor grade was evaluated using the Nottingham system [Elston and Ellis, (1991)]. Immunohistochemical evaluation was performed on paraffin-embedded tumor samples obtained at diagnosis and at definitive surgery. Staining of bcl2, p53, ER, progesterone receptor (PgR), and Ki67 were performed at the Pathology Unit of the Azienda Ospedaliera Istituti Ospitalieri of Cremona (Italy), and MN/CA IX staining was assessed at the John Radcliffe Hospital in Oxford, UK.

The immunohistochemical methodology used in Cremona for routine markers is completely described elsewhere [Bottini et al., (2000)]. Briefly, an antigen retrieval step was performed by heating a tissue section in a citrate buffer. The primary antibodies applied were: ER [mouse monoclonal 6F11 (Novocastra Lab., UK), dilution 1:50, 1 h incubation at room temperature], PgR [mouse monoclonal 1A6 (Novocastra Lab.), dilution 1:20, 1 h incubation at room temperature], Ki67 [mouse monoclonal Mib-1 (Dako, Glostrup, Denmark), dilution 1:30, 1 h incubation at room temperature], p53 [mouse monoclonal D07 (Novocastra Lab.), dilution 1:100, 1 h incubation at room temperature], bcl2 [mouse monoclonal 124 (Dako), dilution 1:40, overnight incubation at 4° C.], and c-erbB2 [mouse monoclonal CB11 (Novocastra Lab.), overnight incubation at 4° C.].

Biotinylated horse anti-mouse IgG and avidin-biotin-peroxidase complex were applied as a staining method (Vectastatin ABC kit; Vector Laboratories, Inc., Burlingame, Calif., USA). A solution containing hydrogen peroxide (0.06% v/v) and diamino-benzidine-4 HCl (DAB; 0.05 v/v) was used as chromogen.

All samples had a negative control slide (no primary antibody) of an adjacent section to assess the degree of non-specific staining. Positive controls included breast carcinomas known to exhibit high levels of each marker.

All staining was scored by counting the number of positive-stained cells and was expressed as a percentage of the total tumor cells (at least 1000) counted across several representative fields of the section using a standard light microscope equipped with a 10×10 square graticule. Reproducibility of counting was assessed by a second investigator re-scoring ten slides.

The relative intensity of ER and PgR staining was assessed in a semi-quantitative fashion as previously described by McCarty et al. (1985), incorporating both the intensity and distribution of specific staining. A value (HSCORE) was derived from the sum of the percentages of positive-stained epithelial cells multiplied by the weighted intensity of staining. Specimens were deemed receptor positive if the HSCORE was greater than 100.

Immunohistochemistry for MN/CA IX was performed on tissues retrieved from the histopathology archives at the Pathology Unit of Cremona, Italy. Two core tissue biopsies, 0.6 mm in diameter, were taken from selected morphologically representative regions of each paraffin-embedded breast tumor and sections of 5 µm thickness of each tissue array block were transferred to the glass slides. Quality control was assessed on each block by haepatoxylin and eosin (H&E) staining.

Immunohistochemical staining for the endogenous hypoxia marker CA IX was performed with the murine monoclonal antibody M75, supra at a dilution of 1:50 for 30 min [Pastorekova et al., (1992); ATCC deposited VU-M75 hybridoma, supra]. Secondary antibody, an anti-rabbit anti-mouse antibody complex from the EnVision™ HRP kit (Dako) was allowed to incubate for 30 min. Slides were then stained with DAB and counterstained with hematoxylin and mounted. The immunostaining was quantified in carcinoma cells by semi-quantitative scoring as previously described [Colpaert et al., (2003)]. In brief, a score of 0-2 for the intensity of staining was given (0, no staining; 1, weak staining; 2, moderate to strong staining). For all comparisons with survival and response, any staining was counted as positive.

The pathologists performing the immunohistochemical evaluations both in the Pathology Unit of Cremona, Italy and John Radcliffe Hospital in Oxford, UK worked in blinded conditions, that is, they did not know the patient outcome and whether the samples they examined were obtained from incisional biopsy or definitive surgery.

Statistical methodology: The $x^2$-test for trend and Fisher's exact test were used when indicated to perform comparisons of proportions. Kruskal-Wallis ANOVA was performed to compare continuous variables. Multivariate logistic regression was used to identify covariates independently associated with MN/CA IX expression. In this analysis, MN/CA IX expression was dichotomized in two classes, '0' (no immunostaining) and '1' (presence of immunostaining). DFS was calculated from randomization to the occurrence of disease relapse or death, whichever was first. Overall survival (OS) was calculated from randomization to the date of death. The last follow-up date was considered for DFS and OS (censored), if patients were free from recurrence and alive respectively. The DFS and OS curves were estimated using the Kaplan-Meier method. Unadjusted differences in these estimates were assessed with the log rank test. The Cox proportional hazard model was used to assess the independent predictive role of the clinical-pathological factors in multivariate analysis, and the treatment undergone for disease recurrence. The analysis was conducted in two steps: initially, MN/CA IX expression and all classical clinical and pathological factors were included in the multivariate model. Variables not significantly associated with the outcome were then removed from the model in a stepwise backward procedure based on the likelihood ratio (P<0.10). In the second step, the presence of interactions between MN/CA IX and each of the clinical and pathological factors and the treatment undergone was investigated by introducing the appropriate terms describing the interaction between the MN/CA IX and the covariates of interest, one at a time, in the final model obtained in the preceding step. Due to the small sample size and the number of interactions that were evaluated, these analyses must be considered as exploratory, and no attempt was made to build a complete model, where all the significant interaction terms and the associated main effects were included and evaluated simultaneously. All variables included in multivariate analyses were dichotomized and coded '0' in negative cases and '1' in positive cases with the exception of Ki67. This latter variable had a left skewed distribution and was modeled using the log transformation. The assumption of proportional hazards was verified by visual inspection of the plots of the log-estimated cumulative hazards in the various strata defined by the covariates, and no major violation of the assumption was observed. All P values reported were two sided; values less than 0.05 were considered statistically significant.

Statistical analyses were performed using the STATISTICA for Windows (Tulsa, Okla., USA) and SPSS for Windows software packages.

EXAMPLE 1

Patient Characteristics and MN/CA IX Expression

The purpose of this study is to investigate the role of carbonic anhydrase IX (MN/CA IX) expression in predicting the response to epirubicin and disease-free survival (DFS) in breast cancer patients enrolled in a single institution trial of primary anthracycline and tamoxifen therapy. MN/CA IX expression was assessed in 183 patients with T2-4 N0-1 breast cancer enrolled in a randomized trial comparing four cycles of single agent epirubicin versus epirubicin+tamoxifen as primary systemic treatment. All patients received postoperatively four cycles of the four weekly i.v. cyclophosphamide, methotrexate, 5-fluorouracil regimen. Patients with estrogen receptor (ER)-positive primary tumors received 5 years of adjuvant tamoxifen. Pretreatment, p53 (P=0.007), c-erbB2 (P<0.01), and Ki67 (P=0.02) were directly associated with MN/CA IX expression, while bcl2 (P<0.000) and ER (P=0.000) and progesterone receptor (PgR; P<0.01) were inversely correlated. In multivariate analysis, only high p53 and low bcl2 were independently associated with MN/CA IX positivity. MN/CA IX immunostaining was significantly associated with poor outcome for DFS (P<0.002) and overall survival (P=0.001). In multivariate analysis, a significant interaction was found between MN/CA IX and markers of hormone sensitivity, bcl2 (P=0.01), ER (P=0.02), PgR (P=0.02), and lymph node involvement (P=0.04), in predicting DFS.

Presently, there are few clinical markers of resistance to tamoxifen treatment in ER-positive tumors. MN/CA IX expression in breast cancer patients shows a negative predictive role of treatment efficacy in ER-positive patients on the adjuvant tamoxifen after primary chemo-endocrine therapy.

Out of 211, 183 patients prospectively enrolled in the trial (86.7%) had MN/CA IX assessed. For the remaining 28 patients, the blocks had been discarded due to insufficient material. Characteristics of the 183 patients included in this study are shown in Table 1. Eighty-nine patients were randomized in the EPI arm, ninety-four were randomized in the EPI-TAM arm. One hundred and sixty-nine patients had MN/CA IX evaluated at the baseline, one hundred and forty had MN/CA IX assessed in residual tumor, one hundred and twenty-six had MN/CA IX assessed both before and after treatment, while fourteen patients had MN/CA IX assessed in the residual tumor histology only. MN/CA IX immunostaining was detected in 41/169 tumor samples collected before treatment (24.2%) and in 30/140 tumor samples collected afterwards (21.4%).

TABLE 1

Patient characteristics

| | | |
|---|---|---|
| No. of randomized | | 183 |
| EPI | | 89 |
| EPI-TAM | | 94 |
| Premenopause | | 61 (33.9%) |
| Postmenopause | | 119 (66.1%) |
| Grading | | |
| 1 | | 0 |
| 2 | | 47 (26.5%) |
| 3 | | 131 (73.5%) |
| Missing | | 5 |
| T stage | | |
| T2 | | 138 (75.4%) |
| T3 | | 26 (14.2%) |
| T4 | | 19 (10.4%) |
| N status | | |
| N0 | | 104 (56.8%) |
| N1 | | 79 (43.2%) |
| ER− | | 38 (20.7%) |
| ER+ | | 145 (79.2%) |
| PgR− | | 92 (50.3%) |
| PgR+ | | 91 (49.7%) |
| p53− | | 91 (50.0%) |
| p53+ | | 91 (50.0%) |
| Missing | | 1 |
| c-erbB2− | | 134 (73.2%) |
| c-erbB2+ | | 49 (26.8%) |
| bcl2− | | 50 (27.5%) |
| bcl2+ | | 132 (72.5%) |
| Missing | | 1 |
| Response to treatment (clinical) | | |
| Complete response | | 32 (17.6%) |
| Partial response | | 108 (59.3%) |
| No response | | 42 (23.1%) |
| Not evaluable | | 1 |
| Pathological complete response | | 6 (3.3%) |
| Baseline | | |
| CA IX (n = 169) | 0 | 128 (75.7%) |
| | 1 | 20 (11.8%) |
| | 2 | 21 (12.5%) |
| After treatment | | |
| CA IX (n = 140) | 0 | 110 (78.6%) |
| | 1 | 17 (12.1%) |
| | 2 | 13 (9.3%) |

EXAMPLE 2

Relationship Between MN/CA IX Expression and Clinical and Immunohistochemical Prognostic Parameters As shown in Table 2, MN/CA IX expression at baseline conditions did not correlate with T status and N status in univariate analysis. An association of borderline significance (0.08) between MN/CA IX intensity and grade was observed. MN/CA IX expression was directly associated with p53, c-erbB2, and Ki67 expression, while it was inversely associated with bcl2 and steroid hormone receptor status.

In multivariate analysis, however, the only two variables independently associated with MN/CA IX positivity were bcl2 expression, [odds ratio (OR) 0.2; 95% confidence interval (CI): 0.1-0.5, P=0.0001], and p53 expression [OR 2; 95% CI: 0.9-4.8, P=0.05].

TABLE 2

Relationship between baseline MN/CA IX expression and clinical and immunohistochemical parameters

| CA IX intensity Grading | 0 | 1 | 2 | P |
|---|---|---|---|---|
| 2 | 36/125 (28.8%) | 7/20 (35.0%) | 1/19 (5.3%) | |
| 3 | 89/125 (71.2%) | 13/20 (65.0%) | 18/19 (94.7%) | 0.08* |
| p53 | 56/128 (43.7%) | 14/20 (70.0%) | 14/20 (70.0%) | 0.007* |
| c-erbB2 | 48/128 (37.5%) | 13/20 (65.0%) | 13/21 (61.9%) | <0.01* |
| bcl2 | 105/127 (82.6%) | 14/20 (70.0%) | 6/21 (28.6%) | 0.000* |
| ER | 111/128 (86.7%) | 15/20 (75.0%) | 11/21 (52.4%) | 0.000* |
| PgR | 71/128 (55.5%) | 7/20 (35.0%) | 6/21 (28.6%) | <0.01* |
| Ki67 mean (95% CI) | 19.8 (17.1-22.5) | 26.0 (13.6-38.5) | 35.8 (23.2-48.5) | 0.02 |
| T2 | 98/128 (76.5%) | 13/20 (65.0%) | 16/21 (76.2%) | |
| T3-4 | 30/128 (23.5%) | 7/20 (35.0%) | 5/21 (23.8%) | 0.68 |
| N+ | 53/128 (41.4%) | 10/20 (50.0%) | 11/21 (52.4%) | 0.12* |

| Multivariate analysis† | Odds ratio | 95% confidence intervals | P |
|---|---|---|---|
| *Variables in the model* | | | |
| p53 | 2 | 0.9-4.8 | 0.05 |
| bcl2 | 0.2 | 0.1-0.5 | 0.0001 |
| *Variables failing to enter the model* | | | |
| ER | 0.9 | 0.2-3.1 | 0.6 |
| Tumor grade | 0.9 | 0.3-2.4 | 0.9 |
| PgR | 0.6 | 0.2-1.6 | 0.2 |
| Log Ki67 | 1 | 0.5-1.9 | 0.7 |
| c-erbB2 | 1.7 | 0.7-4.1 | 0.17 |

*$X^2$ for trend;
†CA IX was dichotomized and coded as '0' (no expression) and '1' (expression).

EXAMPLE 3

Effect of Treatment on MN/CA IX Immunostaining

In 126 patients with MN/CA IX assessed in matched samples before and after treatments, MN/CA IX positivity was found in 32 baseline tumor samples (25.4%) and 27 residual tumor samples to chemotherapy (21.4%), respectively. MN/CA IX-positive tumors (21/32) at the baseline showed reduction in marker expression (Table 3), and 18 of these became negative at the end of treatment, while MN/CA IX-negative tumors (13/94) at the baseline became positive at the end of treatment. MN/CA IX variation did not differ according to the treatment received (EPI or EPI-Tam; data not shown).

TABLE 3

MN/CA IX individual changes and MN/CA IX expression before and after treatment

| | Overall | No variation | Increase | Decrease |
|---|---|---|---|---|
| CA IX + ve | 32 | 11 (34.4%) | n.a. | 21 (65.6%) |
| CA IX − ve | 94 | 81 (86.2.%) | 13 (13.8%) | n.a. |

EXAMPLE 4

MN/CA IX Expression and Response to Treatment

Among 169 patients with MN/CA IX assessed at baseline, one patient refused to continue the treatment after the first cycle and was not assessable for response; 129 (76.7%) out of 168 assessable cases attained a clinical response (complete+ partial), 30 (17.8%) cases showed a CR, and 99 (58.9%) had a PR. At postchemotherapy residual histology, six patients (3.6%) had a pCR. As previously published, there was no significant difference in treatment responses between the epirubicin and epirubicin+tamoxifen arms (76 vs 82% respectively) [Bottini et al., (2005)]. According to the MN/CA IX status, overall response was observed in 100 out of 127 patients (78.7%) with MN/CA IX-negative tumors and 29 out of 41 patients (70.7%) with MN/CA IX-positive tumors, and CR was observed in 25/127 (19.7%) MN/CA IX-negative and in 5/41 (12.2%) MN/CA IX-positive patients respectively. None of these differences was statistically significant. All the six pCRs were confined to patients with MN/CA IX negative primary tumor (P=0.33, Fisher's exact test).

EXAMPLE 5

MN/CA IX Expression and Disease Outcome

Out of 183, 45 patients relapsed (24.6%), and 21 (11.5%) died of disease. As shown in FIGS. 1A and B, MN/CA IX expression was significantly associated with poor outcome both in terms of DFS and OS. In univariate analysis, tumor grade (P=0.04), T (P=0.0001) and N status (P=0.000), ER (P=0.003), PgR (P=0.03), and bcl-2 expression (P=0.002), in addition to MN/CA IX expression, were significantly associated with disease recurrence, while the correlation with disease recurrence of Ki67 (P=0.10), p53 (P=0.06), and c-erbB2 expression (P=0.07) just failed to attain statistical significance. Menopausal status was not associated with disease recurrence (P=0.29).

In multivariate analysis, MN/CA IX expression was not an independent predictor of DFS (Table 4). Tumor size [hazard ratio (HR) 2.7; 95% CI: 1.4-5.4, P=0.003], lymph node involvement (HR 2.8; 95% CI: 1.4-5.7, P=0.004), and bcl2 status (HR 0.4; 95% CI: 0.2-0.8, P=0.008) were retained in the final model. Treatment-induced changes in MN/CA IX were not correlated with DFS in univariate analysis (data not shown).

TABLE 4

Multivariate Cox analysis for independent factors predictive for disease recurrence

| | Hazard ratio | 95% confidence intervals | P |
|---|---|---|---|
| Variables in the final model | | | |
| Nodal status | 3.0 | 1.5-6.0 | 0.002 |
| T | 2.6 | 1.3-5.0 | 0.007 |
| bcl2 | 0.4 | 0.2-0.8 | 0.008 |
| Variables failing to enter the model | | | |
| c-erbB2 | 0.7 | 0.3-1.5 | 0.4 |
| PgR | 1.1 | 0.5-2.6 | 0.8 |
| ER | 0.7 | 0.3-1.9 | 0.5 |
| Grading | 1.4 | 0.5-3.8 | 0.4 |
| Log Ki67 | 2.5 | 0.8-8.0 | 0.1 |
| CA IX | 1.6 | 0.8-3.2 | 0.2 |
| p53 | 1.2 | 0.6-2.4 | 0.5 |

EXAMPLE 6

Figure 2:
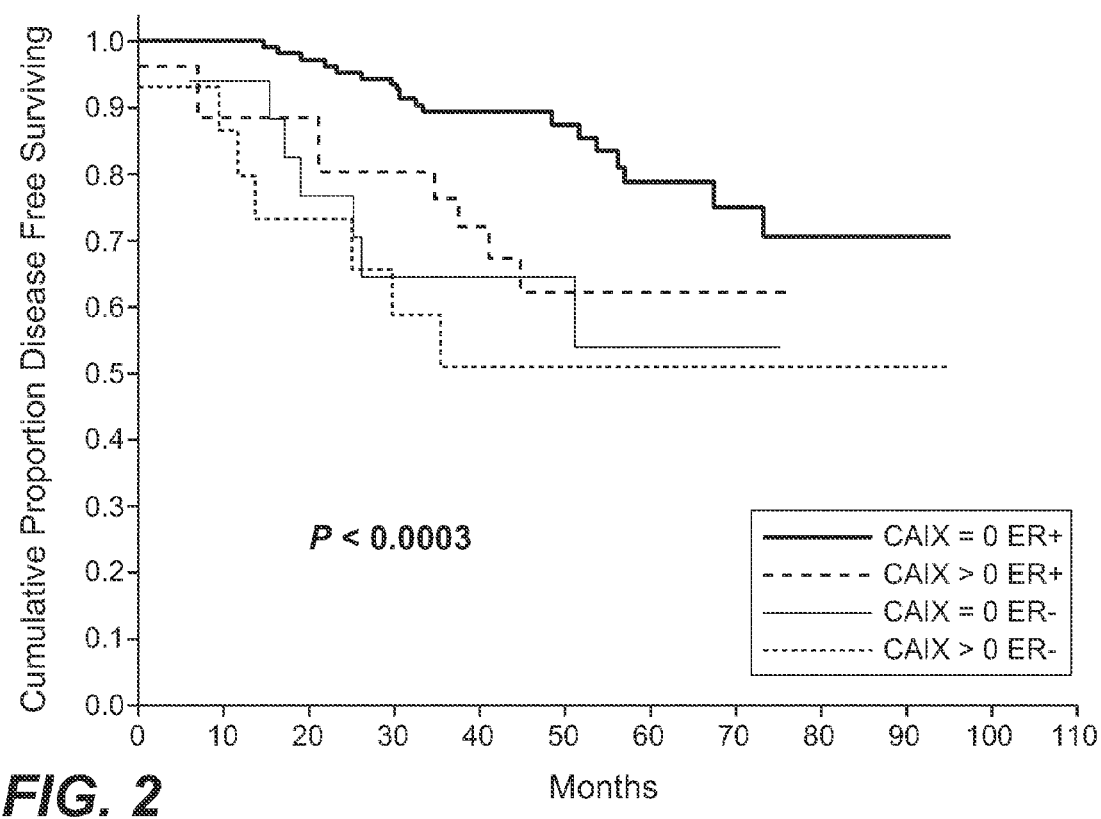
FIG. 2 graphically depicts disease-free survival of breast cancer patient subgroups stratified according to CA IX and estrogen receptor (ER) status.

Effect of MN/CA IX on DFS in Different Subgroups According to Clinical and Pathological Parameters In the exploratory analyses aimed at evaluating the interactions on DFS between MN/CA IX and each of the clinical and pathological parameters, a significant positive interaction was found between MN/CA IX and bcl2 (P=0.01), ER (P=0.02), PgR (P=0.02), and lymph node involvement (P=0.04). The interaction between MN/CA IX and the various factors in predicting DFS is depicted in Table 5. As shown, MN/CA IX positivity was clearly associated with a two- to threefold increased risk of relapse in patients with tumors positive for markers of responsiveness to endocrine therapy, such as ER, PgR and bcl2, and in node-positive patients, whereas no association was seen in patients negative for these markers and in node-negative patients (Table 5). No variation in the prognostic effect of MN/CA IX was seen across subgroups of the other factors. The interaction between MN/CA IX and ER status is shown in FIG. 2 in which the predictive role of MN/CA IX for DFS in univariate analysis is confined to ER-positive patients.

TABLE 5

Subgroup analysis of disease-free survival of MN/CA IX-positive patients versus MN/CA IX negative ones within strata formed by each prognostic factor

| | Hazard ratio* | 95% confidence interval | P |
|---|---|---|---|
| Estrogen receptor | | | |
| Positive | 3.2 | 1.4-7.4 | 0.02† |
| Negative | 0.7 | 0.2-3.1 | |
| Progesterone receptor | | | |
| Positive | 17.1 | 3.2-90.5 | 0.02† |
| Negative | 1.0 | 0.4-2.6 | |

TABLE 5-continued

Subgroup analysis of disease-free survival of MN/CA IX-positive patients versus MN/CA IX negative ones within strata formed by each prognostic factor

| | Hazard ratio* | 95% confidence interval | P |
|---|---|---|---|
| bcl2 | | | |
| Positive | 2.8 | 1.1-7.1 | 0.01† |
| Negative | 0.6 | 0.2-1.9 | |
| Node status | | | |
| Positive | 2.2 | 1.0-4.8 | 0.04† |
| Negative | 1.1 | 0.2-4.4 | |

*From a Cox model in which all variables were included as covariates.
†Test for interaction. The interaction terms were, one at a time, added to the final model. Before testing another interaction, both the covariate and the interaction term were removed from the model. Terms for interaction of MN/CA IX with p53, tumor grade, log Ki67, c-erbB2, and T status were not significantly associated with outcome and were not included in the table.

Discussion

Hypoxia has been implicated as an important component in tumor progression and spread. MN/CA IX was initially identified to be hypoxia inducible in several epithelial cell lines, and its expression was closely correlated with the presence of necrosis, believed to be an indicator of local hypoxia, within invasive breast tumors [Leek et al. (1999)]. As a measure of tumor cell hypoxia, MN/CA IX was shown to be a prognostic factor in different cancers [Koukourakis et al. (2001)], Loncaster et al. (2001), Hui et al., (2002), Swinson et al. (2003), Bui et al. (2004), Hussain et al. (2004)]. Studies have also revealed that MN's expression is restricted to the transformed, dysplastic, and malignant epithelial cells and is rarely expressed in benign or normal tissue.

However, in the studies published to date, MN/CA IX was assessed in tumor samples of patients submitted to heterogeneous adjuvant treatments or no treatment at all after surgery. From such studies, it is very difficult to draw conclusions on MN's predictive role on treatment efficacy, and the heterogeneous treatments administered could have lead to biased results with respect to the disease outcome, while predictive factors can be best evaluated in the context of a prospective randomized clinical trial. In the experiments disclosed herein, the MN/CA IX evaluation was performed in a series of patients prospectively enrolled in a single institution phase III trial comparing epirubicin versus epirubicin+tamoxifen, as primary systemic treatment [Bottini et al. (2005)]. In addition, after surgery, all patients received i.v. CMF regimen in adjuvant setting, and those patients with ER-positive primary tumor in both treatment arms underwent 5 year adjuvant tamoxifen therapy. As previously observed, the MN/CA IX expression was not related to disease stage [Chia et al. (2001)], whereas it was significantly associated with biological tumor prognostic features, such as p53, Ki67, c-erbB2 expression as well as negative steroid hormone receptor status, and negative bcl2 status [Leek et al. (1999)]. Bartosova et al. (2002) reported a weak, but significant, correlation of MN/CA IX in breast cancer with c-erbB2 expression. The present study confirmed that association, and also provides evidence that MN/CA IX with its reversed correlation with ER status and positive correlation with c-erbB2 is associated with resistance to endocrine therapy.

The present experiments are the first to show that MN/CA IX expression is related to the expression of genes regulating apoptosis and proliferative activity. As previously reported, all the biological variables considered in this study are reciprocally correlated [Bottini et al. (2000)]. When the variables associated with MN/CA IX expression in univariate analysis were included in a multivariate logistic regression model, only p53 and bcl2 showed an independent relationship with MN/CA IX expression. The relationship reflects the inverse association with ER, since bcl2 is an estrogen-regulated gene, and p53 expression is associated with ER-negative cases.

Tumor hypoxia regulates many changes in gene expression. In particular, hypoxia selects for p53-mutations [Schmid et al. (2004)] (most p53 detected by immunohistochemical procedures is usually the mutated form) leading to apoptosis inhibition. The direct relationship between MN/CA IX and p53 supports these data, and in cell lines, it has been shown that wild-type p53 suppresses MN/CA IX expression [Kaluzova et al. (2004)], thus providing a mechanism for co-expression in some cases, although most MN/CA IX-positive cases were p53 negative. The inverse relationship with bcl2 reflects the regulation of bcl2 by ER, with hormone receptors being reciprocally related to MN/CA IX.

In this study, MN/CA IX was not predictive of clinical response overall, although no patient with a MN/CA IX-positive tumor had a pCR. The patients were given the maximal dose of epirubicin that can be given without marrow support or cardioprotection on a three weekly basis, as a single agent. The hypothesis tested was that MN/CA IX could mediate one mechanism of resistance relating to poor drug uptake. There was no difference in response in those treated by epirubicin alone versus tamoxifen. Although an effect of MN/CA IX expression was not detected on response, this may be difficult because of the large tumor mass, and effects on elimination of micrometastases could be a more relevant endpoint and represented by poorer DFS.

Few tumors changed the MN/CA IX status before and after treatment. The number of patients with a MN/CA IX-negative tumor at baseline, which becomes positive afterwards is similar to that of patients showing an opposite pattern. The percentage of patients with MN/CA IX-positive tumors did not differ significantly before and after treatment. These data suggest that, as a whole, MN/CA IX immunostaining is not influenced by treatment.

In this series, MN/CA IX expression was significantly associated with poor DFS and OS, confirming previous observations in breast cancer [Chia et al. (2001), Colpaert et al. (2003), Span et al. (2003)]. However, in multivariate analysis, MN/CA IX failed to be an independent predictor of DFS when adjusted for T status, N status, p53, bcl2, Ki67, steroid hormone receptors, and treatment. This observation is in contrast with previous publications [Chia et al. (2001), Span et al. (2003), Chia and Yorida (2004)]. It should be noted, however, that the HR of 1.6 obtained with MN/CA IX in the present study is superimposable to HRs of MN/CA IX reported in multivariate analyses performed in previous studies [Chia et al. (2001), Chia and Yorida (2004), Yorida et al. (2004)]. These data provide further information in favor of the negative prognostic significance of MN/CA IX expression.

A statistical interaction of MN/CA IX was observed with ER, PgR, and bcl2 in determining DFS, indicating that MN/CA IX prognostic significance is limited to (or more pronounced in) patients with hormone-responsive tumors. Hypoxia can cause endocrine therapy resistance as has been shown recently in cell lines in the tissue culture [Cooper et al. (2004), Coradini et al. (2004)], thereby contributing to increased drug resistance. Tamoxifen in particular is a weak basic drug ($pK_a$=8.8), so that possible mechanisms of hypoxia-induced resistance to this drug relate to the acid outside pH gradients that reduce the partitioning of weak basic drugs into the relatively alkaline cells. This phenomenon has its basis in 'ion trapping', wherein weak bases partition into, and are sequestered by acidic compartments, such as the extracellular matrix [Roos (1978)]. This occurs because uncharged, organic-free bases are more permeable than their protonated and charged counterparts and establish equal concentrations on either side of the cell membrane [Gillies (1978)]. There is evidence that decreased uptake is a possible mechanism of resistance in hormone-resistant breast cancers on tamoxifen therapy, although how this occurred was not described [Dowsett et al. (1995)]. The results suggest a contribution of MN/CA IX expression in the tamoxifen resistance. Since the patient population with ER-positive tumors was homogeneously submitted to 5 year adjuvant tamoxifen in addition to chemotherapy, it is not possible to assess whether the observed interaction is due to an antagonizing effect of MN/CA IX positivity on the efficacy of tamoxifen, or it may be attributable to a true interaction between two different tumor characteristics.

In conclusion, there are presently few clinical markers of resistance to tamoxifen treatment in ER-positive tumors. MN/CA IX expression in breast cancer patients shows a negative predictive role of treatment efficacy in ER-positive patients, particularly in the case of adjuvant tamoxifen after primary chemo-endocrine therapy, and is considered to be predictive of resistance to endocrine therapy in ER-positive breast cancer patients.

Budapest Treaty Deposits

The materials listed below were deposited with the American Type Culture Collection (ATCC) now at 10801 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

|  | Deposit Date | ATCC # |
|---|---|---|
| Hybridoma |  |  |
| VU-M75 | Sep. 17, 1992 | HB 11128 |
| MN 12.2.2 | Jun. 9, 1994 | HB 11647 |
| Plasmid |  |  |
| A4a | Jun. 6, 1995 | 97199 |
| XE1 | Jun. 6, 1995 | 97200 |
| XE3 | Jun. 6, 1995 | 97198 |

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM) at the Laboratorium voor Moleculaire Biologie-Plasmidencollectie (LMBP) at the Universeit Gent, K. L. Ledeganckstraat 35, B-9000 Gent, Belgium [BCCM/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method of predicting resistance to endocrine therapy in a breast cancer patient with an ER-positive breast tumor, comprising:
   (a) obtaining a breast tumor tissue sample from said ER-positive breast cancer patient;
   (b) determining immunologically whether said sample is MN/CA IX-positive, wherein MN/CA IX positivity is indicated by any conventionally detectable MN/CA IX-specific immunohistochemical staining of cells in said sample; and
   (c) correlating a finding of combined ER-positivity in said tumor and MN/CA IX-positivity in said sample with a greater probability of resistance to said endocrine therapy for said ER-positive breast cancer patient than if said tumor were ER-positive and said sample were MN/CA IX-negative.

2. The method of claim 1, wherein said endocrine therapy comprises or consists of the use of an antiestrogen or estrogen lowering drug, or drug that modifies endocrine environment.

3. The method of claim 1, wherein said endocrine therapy is a selective estrogen receptor modulator (SERM), a pure antiestrogen, a steroidal aromatase inhibitor, a nonsteroidal aromatase inhibitor, or estrogen.

4. The method of claim 1, wherein said endocrine therapy is selected from the group consisting of tamoxifen, raloxifene, toremifene, fulvestrant, exemestane, letrozole or anastrozole.

5. The method of claim 2, wherein said antiestrogen is tamoxifen.

6. A method of predicting resistance to endocrine therapy in a breast cancer patient with an ER-positive breast tumor, comprising:
   (a) obtaining a body fluid sample from said ER-positive breast cancer patient;
   (b) immunologically detecting the presence or absence of soluble MN/CA IX in said body fluid sample; and
   (c) correlating a finding of combined ER-positivity in said tumor and detectable soluble MN/CA IX in said body fluid sample with a greater probability of resistance to said endocrine therapy for said ER-positive breast cancer patient than if said tumor were ER-positive and said body fluid sample were MN/CA IX-negative.

7. The method of claim 6, wherein said endocrine therapy comprises or consists of the use of an antiestrogen.

8. The method of claim 7, wherein said antiestrogen is tamoxifen.

9. A method of predicting resistance to an antiestrogen therapy in a breast cancer patient with an ER-positive breast tumor, comprising:
   (a) employing diagnostic/prognostic imaging to detect the presence or absence of MN/CA IX in one or more tumors in said ER-positive breast cancer patient, wherein said imaging comprises the use of labeled MN/CA IX-specific antibodies; and
   (b) correlating a finding of combined ER-positivity in said breast tumor and the presence of MN/CA IX in said one or more tumors with a greater probability of resistance to said antiestrogen therapy for said ER-positive breast cancer patient than if said breast tumor were ER-positive and said one or more tumors were MN/CA IX-negative.

10. The method of claim 9, wherein said one or more tumors is or are metastatic tumor(s).

11. A method for selecting an appropriate therapy for a breast cancer patient with an ER-positive breast tumor, comprising:
   (a) immunologically detecting the presence or absence of MN/CA IX in said ER-positive tumor or in a metastasis of said tumor;
   (b) correlating a finding of combined ER-positivity in said breast tumor and the presence of MN/CA IX in said tumor or said metastasis with a greater probability of resistance to antiestrogen therapy for said ER-positive breast cancer patient, than if said breast tumor were ER-positive and said tumor or said metastasis were MN/CA IX-negative; and
   (c) selecting an additional or alternative therapy to antiestrogen therapy for said ER-positive, MN/CA IX-positive breast cancer patient identified in step (b) as having a greater probability of resistance to antiestrogen therapy.

12. The method of claim 11, wherein said antiestrogen therapy is tamoxifen.

13. The method of claim 11, wherein said MN/CA IX comprises soluble MN/CA IX antigen (s-CA IX), a MN protein or a MN polypeptide.

14. The method of claim 11, wherein said additional or alternative therapy is an anthracycline.

15. The method of claim 14, wherein said anthracycline is epirubicin or doxorubicin.

16. The method of claim 11, wherein said additional or alternative therapy is not substantially inhibited by acidic pH.

17. The method of claim 11, wherein said additional or alternative therapy is selected from adjuvant chemotherapy, alternative endocrine therapy, or MN-targeted therapy.

18. The method of claim 17, wherein said adjuvant chemotherapy is a taxane.

19. The method of claim 18, wherein said taxane is paclitaxel or docetaxel.

20. The method of claim 12, wherein if MN/CA IX is present in said tumor or said metastasis, said method further comprises deciding not to use chemotherapy or alternative endocrine therapy substantially inhibited by acidic pH.

21. A method of predicting resistance to tamoxifen in a breast cancer patient with an ER-positive breast tumor, comprising:
   (a) obtaining a breast tumor tissue sample from said ER-positive breast cancer patient;
   (b) immunologically detecting MN/CA IX overexpression in said sample, wherein any conventionally detectable MN/CA IX-specific immunohistochemical staining of cells in said sample indicates MN/CA IX overexpression; and
   (c) correlating a finding of combined ER-positivity in said tumor and MN/CA IX overexpression in said sample with a greater probability of resistance to tamoxifen for said ER-positive breast cancer patient than if said sample were MN/CA IX-negative, and identifying said ER-positive, MN/CA IX-positive breast cancer patient as a candidate for an additional or alternative therapy to tamoxifen.

22. The method of claim 9, wherein said imaging is positron emission tomography (PET) imaging.

23. The method of claim 22, wherein the MN/CA IX-specific antibodies are labeled using the fluorine isotope $^{18}$F.

24. A method of predicting resistance to endocrine therapy in a breast cancer patient with an ER-positive breast tumor, comprising:
   (a) obtaining a breast tumor tissue sample from said ER-positive breast cancer patient;
   (b) determining by MN/CA IX-specific immunohistochemical staining of cells in said sample an MN/CA IX immunoreactivity score of said sample, wherein said sample is assigned an immunoreactivity score with a value of 0 (zero) if no staining,
a value of 1 if weak staining, or
a value of 2 if strong staining;
and
(c) correlating a finding of combined ER-positivity in said tumor and an MN/CA IX immunoreactivity score of the sample greater than 0 (zero), with a greater probability of resistance to said endocrine therapy for said ER-positive breast cancer patient, than if said tumor were ER-positive and said sample had an MN/CA IX immunoreactivity score of 0 (zero).

* * * * *

UNITED STATES PATENT AND TRADEMARK OFFICE
CERTIFICATE OF CORRECTION

PATENT NO. : 8,097,423 B2  
APPLICATION NO. : 12/181951  
DATED : January 17, 2012  
INVENTOR(S) : Adrian L. Harris Page 1 of 1

It is certified that error appears in the above-identified patent and that said Letters Patent is hereby corrected as shown below:

ON THE TITLE PAGE:  
Before Foreign Application Priority Data: add

-- Related U.S. Application Data

(60) Provisional application No. 60/952,809 filed on July 30, 2007. --

IN THE SPECIFICATIONS:

Column 1, Line 1 after the title insert -- This application claims the benefit of U.S. Provisional Application No. 60/952,809, filed July 30, 2007. --

Signed and Sealed this  
Thirtieth Day of April, 2013

Teresa Stanek Rea  
*Acting Director of the United States Patent and Trademark Office*